(12) United States Patent
Lee et al.

(10) Patent No.: US 12,006,592 B2
(45) Date of Patent: *Jun. 11, 2024

(54) VASCULAR CONSTRUCTS

(71) Applicant: Wake Forest University Health Sciences, Winston-Salem, NC (US)

(72) Inventors: Sang Jin Lee, Winston-Salem, NC (US); James J. Yoo, Winston-Salem, NC (US); Young Min Ju, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 525 days.

This patent is subject to a terminal disclaimer.

(21) Appl. No.: 17/316,342

(22) Filed: May 10, 2021

(65) Prior Publication Data
US 2021/0269943 A1 Sep. 2, 2021

Related U.S. Application Data

(63) Continuation of application No. 16/171,504, filed on Oct. 26, 2018, now Pat. No. 11,028,502.
(Continued)

(51) Int. Cl.
*D01D 5/00* (2006.01)
*A61K 31/728* (2006.01)
(Continued)

(52) U.S. Cl.
CPC .......... *D01D 5/003* (2013.01); *A61K 31/728* (2013.01); *A61K 31/729* (2013.01); *A61K 31/737* (2013.01); *A61K 35/44* (2013.01); *A61K 38/1858* (2013.01); *A61K 38/363* (2013.01); *A61K 38/39* (2013.01); *A61L 27/24* (2013.01);
(Continued)

(58) Field of Classification Search
CPC .... D01D 5/003; A61K 31/728; A61K 31/729; A61K 31/737; A61K 35/44; A61K 38/1858; A61K 38/363; A61K 38/39; A61L 27/24; A61L 27/3826; A61L 27/58; A61L 27/3834; A61L 27/54; A61L 31/044;
(Continued)

(56) References Cited

U.S. PATENT DOCUMENTS 7,531,503 B2 * 5/2009 Atala ................. B82Y 5/00
                                                  514/23
7,615,373 B2 * 11/2009 Simpson ............. A61L 27/3839
                                                  623/23.72

(Continued)

OTHER PUBLICATIONS

B.W. Tillman, S.K. Yazdani, S.J. Lee, R.L. Geary, A. Atala, J.J. Yoo, The in vivo stability of electrospun polycaprolactone-collagen scaffolds in vascular reconstruction, Biomaterials 30(4) (2009) 583-8.
(Continued)

*Primary Examiner* — Suzette J Gherbi
(74) *Attorney, Agent, or Firm* — Reza Mollaaghababa; Joseph F. Murphy; Potomac Law Group, PLLC

(57) ABSTRACT

The invention is directed to products and methods for preparing self-seeding vascular constructs generated as a bi-layered electrospun matrices, conjugated with EPC-specific antibodies and anti-thrombogenic agents on the inner surfaces of their lumens.

36 Claims, 17 Drawing Sheets

Related U.S. Application Data

(60) Provisional application No. 62/580,770, filed on Nov. 2, 2017.

(51) Int. Cl.
| | | |
|---|---|---|
| *A61K 31/729* | (2006.01) | |
| *A61K 31/737* | (2006.01) | |
| *A61K 35/44* | (2015.01) | |
| *A61K 38/18* | (2006.01) | |
| *A61K 38/36* | (2006.01) | |
| *A61K 38/39* | (2006.01) | |
| *A61L 27/24* | (2006.01) | |
| *C07D 315/00* | (2006.01) | |
| *C07K 16/18* | (2006.01) | |
| *C07K 16/28* | (2006.01) | |
| *C07K 16/46* | (2006.01) | |
| *D01F 1/10* | (2006.01) | |
| *D01F 6/92* | (2006.01) | |
| *D01F 4/00* | (2006.01) | |
| *D01F 6/62* | (2006.01) | |

(52) U.S. Cl.
CPC ............ *C07D 315/00* (2013.01); *C07K 16/18* (2013.01); *C07K 16/289* (2013.01); *C07K 16/46* (2013.01); *D01D 5/0076* (2013.01); *D01F 1/10* (2013.01); *D01F 6/92* (2013.01); *C07K 16/2896* (2013.01); *D01F 4/00* (2013.01); *D01F 6/625* (2013.01)

(58) Field of Classification Search
CPC .......... A61L 31/148; A61L 31/16; D01F 6/92; D01F 4/00; D01F 6/625; C07K 16/2896
See application file for complete search history.

(56) References Cited

U.S. PATENT DOCUMENTS

| | | | | |
|---|---|---|---|---|
| 8,491,457 | B2* | 7/2013 | Atala | A61K 35/44 435/395 |
| 9,163,331 | B2 | 10/2015 | Atala et al. | |
| 9,522,217 | B2* | 12/2016 | Kutryk | A61L 27/54 |
| 11,866,701 | B2* | 1/2024 | Hinkle | C12N 15/113 |
| 2003/0229393 | A1* | 12/2003 | Kutryk | A61L 31/10 523/113 |
| 2006/0204441 | A1* | 9/2006 | Atala | B82Y 10/00 514/8.4 |
| 2007/0059288 | A1* | 3/2007 | Dinsmore | A61K 38/1841 514/8.1 |
| 2007/0264306 | A1* | 11/2007 | Flameng | A61L 27/3625 424/94.64 |
| 2009/0186065 | A1 | 7/2009 | Tillman et al. | |
| 2010/0331980 | A1* | 12/2010 | Lee | A61L 27/3826 623/14.13 |
| 2015/0112419 | A1 | 4/2015 | Ahn et al. | |
| 2016/0199179 | A1* | 7/2016 | Atala | A61F 2/2415 623/2.42 |
| 2016/0199205 | A1* | 7/2016 | Cottone | A61K 9/0051 623/1.16 |
| 2016/0325010 | A1* | 11/2016 | Liebler | A61L 24/08 |
| 2019/0008664 | A1* | 1/2019 | Sanders | A61F 2/2418 |
| 2019/0060516 | A1* | 2/2019 | Martin | D06M 15/03 |
| 2019/0275195 | A1* | 9/2019 | Leibler | A61L 26/0066 |
| 2020/0054436 | A1* | 2/2020 | Spindler | A61F 2/91 |

OTHER PUBLICATIONS

Brannon-Peppas, Lisa, "Polymers in Controlled Drug Delivery," Medical Plastics and Biomaterials, Nov. 1997.

H. Ahn, Y.M. Ju, H. Takahashi, D.F. Williams, J.J. Yoo, S.J. Lee, T. Okano, A. Atala, Engineered small diameter vascular grafts by combining cell sheet engineering and electrospinning technology, Acta Biomater 16 (2015) 14-22.

Heumanson, Bioconjugate Techniques, Academic Press San Diego, Calif., 1996.

J. Lee, J.J. Yoo, A. Atala, S.J. Lee, Controlled heparin conjugation on electrospun poly(epsilon-caprolactone)/gelatin fibers for morphology-dependent protein delivery and enhanced cellular affinity, Acta Biomater 8(7) (2012) 2549-58.

J. Lee, J.J. Yoo, A. Atala, S.J. Lee, The effect of controlled release of PDGF-BB from heparin-conjugated electrospun PCL/gelatin scaffolds on cellular bioactivity and infiltration, Biomaterials 33(28) (2012) 6709-20.

J. Stitzel, J. Liu, S.J. Lee, M. Komura, J. Berry, S. Soker, G. Lim, M. Van Dyke, R. Czerw, J.J.Yoo, A. Atala, Controlled fabrication of a biological vascular substitute, Biomaterials 27(7) (2006) 1088-94.

J.D. Vossler, Y. Min Ju, J.K. Williams, S. Goldstein, J. Hamlin, S.J. Lee, J.J. Yoo, A. Atala, CD133 antibody conjugation to decellularized human heart valves intended for circulating cell capture, Biomedical materials 10(5) (2015) 055001.

J.E. Jordan, J.K. Williams, S.J. Lee, D. Raghavan, A. Atala, J.J. Yoo, Bioengineered selfseeding heart valves, J Thorac Cardiovasc Surg 143(1) (2012) 201-8.

J.K. Williams, E.S. Miller, M.R. Lane, A. Atala, J.J. Yoo, J.E. Jordan, Characterization of CD133 Antibody-Directed Recellularized Heart Valves, J Cardiovasc Transl Res 8(7) (2015) 411-20.

Kimura et al., (1983) J. Polym. Sci. 21, 2777), enzymes (Chase et al. (1998) Biotechnol. Appl. Biochem., 27, 205), and nucleotides (Overberger et al. (1989) J. Polym. Sci. 27, 3589.

S.J. Lee, J. Liu, S.H. Oh, S. Soker, A. Atala, J.J. Yoo, Development of a composite vascular scaffolding system that withstands physiological vascular conditions, Biomaterials 29(19) (2008) 2891-8.

S.J. Lee, J.J. Yoo, G.J. Lim, A. Atala, J. Stitzel, In vitro evaluation of electrospun nanofiber scaffolds for vascular graft application, J Biomed Mater Res A 83(4) (2007) 999-1008.

Y.M. Ju, J.S. Choi, A. Atala, J.J. Yoo, S.J. Lee, Bilayered scaffold for engineering cellularized blood vessels, Biomaterials 31(15) (2010) 4313-21.

\* cited by examiner

VASCULAR CONSTRUCTS

CROSS-REFERENCE TO RELATED APPLICATIONS

The present application is a continuation of U.S. patent application Ser. No. 16/171,504, filed on Oct. 26, 2018, which claims benefit under 35 U.S.C. 119(e) to U.S. Provisional Application No. 62/580,770, which was filed Nov. 2, 2017, entitled "Vascular Constructs", the contents of which are hereby incorporated by reference in their entirety.

GOVERNMENT INTEREST

This invention was made with U.S. support under Grant No. W81XWH-08-2-0032 awarded by the Armed Forces Institute of Regenerative Medicine (AFIRM) at the U.S. Army Medical Research and Material Command (USAMRMC). The government has certain rights in the invention.

BACKGROUND

The technical field of this invention relates to self-seeding electrospun matrices for cellular attachment and growth. The invention also relates to methods of making and using these matrices for tissue engineering and the construction of vascular constructs, such as artificial blood vessels.

Diseases of small and medium caliber arteries account for the majority of deaths in the United States each year. Over 500,000 coronary bypass grafts and 50,000 peripheral bypass grafts are performed annually in Europe and in the United States. However, up to 30% of the patients who require arterial bypass surgery lack suitable or sufficient amounts of suitable autologous conduits such as small caliber arteries or saphenous veins, which remain the standard conduit for coronary bypass surgery.

Synthetic grafts, such as polytetrafluoroethylene (PTFE) or Dacron (polyethylene terephthalate fiber) have been used to bypass large caliber high-flow blood vessels. However, these grafts fail when used to bypass small-caliber, low flow blood vessels due to increased thrombogenicity and accelerated intimal thickening leading to early graft stenosis and occlusion.

In the last two decades many attempts have been made to engineer functional small-caliber (e.g., less than about 5-6 mm) arterial substitutes. However, these substitutes have been prone to occlusion or have exhibited poor mechanical and/or burst strength, which has precluded in vivo implantation. Accordingly, a need exists for improved constructs for tissue engineering of blood vessels and other vascular structures.

SUMMARY

The present invention provides methods and compositions for preparing self-seeding, tissue engineered vascular constructs, especially blood vessels. Examples of vascular constructs include, but are not limited to coronary vessels for bypass or graft, heart valves. femoral arteries, popliteal arteries, brachial arteries, tibial arteries, radial arteries or corresponding veins.

Functionalized, self-seeding vascular constructs can be made from bi-layer or multi-layer electrospun matrices with an inner layer having an average pore size at the luminal surface that facilitates attachment of progenitor or stem cells, especially endothelial progenitor cells, and/or facilitates growth of the attached cells into a confluent inner epithelial cell ("intima") layer. The outer layer of the vascular construct has a surface with a different average pore size, preferably one that facilitates attachment of smooth muscle cells. The different layers can be achieved by varying electrospinning parameters such that small fibers form the inner layer of the construct while larger fibers form an outer layer. The constructs are also functionalized to enhance autologous cell capture following implantation.

To functionalize the constructs, one or more binding moieties, such as CD133 antibodies, can also be disposed at the inner surface. e.g., by physical integration, chemical linking, or coating. The binding moiety preferably has an affinity for progenitor or stem cells, especially endothelial progenitor cells. Anti-thrombogenic agents, such as heparin, can be similarly disposed at the inner surface of the construct to inhibit blood clotting of the self-seeding constructs following implantation (e.g., during the period that progenitor cells are being captured or endothelial cells are growing into an intima layer). In one preferred embodiment, the binding moieties and/or anti-thrombogenic agents are bio-conjugated to the electrospun matrix by first applying an activation agent to the construct and then applying a solution containing the functionalizing agent. For example the inner surface of the construct can be activated with carbodiimide agent and then a solution containing the functionalizing agent can be applied to the activated surface. In one embodiment. after surface activation, the tubular matrix can be treated with the fluid flow system in which a fluid containing antibodies, e.g., CD133 antibodies and/or anti-thrombogenic agents, such as heparin, are moved through the lumen and deposited on or bound to the construct.

Accordingly, in one aspect, the invention pertains to methods for producing self-seeding, bi-layered blood vessels by providing a electrospun biocompatible matrix shaped in a tubular configuration, having smaller pores on the internal surface and larger pores on the outer surface. Different average pore sizes can be obtained, for example. by variation of one or more electrospinning parameters, such as the size of the ejection nozzle or needle, the flow rate of material and/or the air gap distance. Such variations can change the diameter of the fibers being electrostatically deposited on a spinning mandrel. Deposition of smaller fibers first will result in smaller average pore sizes within the inner layer and subsequent deposition of larger fibers will provide larger average pore sizes in the outer layer. The preferred average fiber diameter for formation of the inner layer ranges from about 1 to about 5 micrometers.

In another aspect of the invention, "off-the-shelf" cell-free vascular grafts are disclosed for repair of small diameter blood vessels. The grafts are bi-layered (or multi-layered) electrospun biocompatible matrices shaped in a tubular configuration, having smaller pores on the internal surface and larger pores on the outer surface. In certain embodiments, the construct can be an electrospun matrix comprising at least one natural component and at least one synthetic polymer component. The natural component can be collagen and the synthetic polymer component can be, for example, a poly($\varepsilon$-caprolactone) (PCL) or a poly(lactide-co-glycolide (PLGA). The electrospun matrix may further include other substances, such as elastin or other extracellular matrix proteins.

In certain embodiments, at least the inner luminal surface or intima of the construct is functionalized with antibodies that have specific binding affinity for endothelial progenitor cells, e.g., CD133 antibodies and/or anti-thrombogenic agents. such as heparin. The constructs can also be coupled with therapeutic agents for controlled delivery of therapeutic agents, and/or coupled with image enhancing agents to monitor the tissue and scaffold remodeling in vivo. The self-seeding blood vessel construct is designed to be ready for implantation where it will self-seed with endothelial cells (EC) on the internal lumen surface and smooth muscle cells (SMC) on the external surface of the vessel.

In another aspect of the invention, functionalized bi-layer constructs can be formed by electrospinning techniques and then alternatively be pre-seeded with endothelial and/or smooth muscle cells. The construct can be formed as a bi-layer or multi-layer matrix and functionalized as described above. A biological fluid containing cells. e.g., autologous endothelial cells and/or smooth muscles obtained from the intended recipient of the construct, can be moved through the tubular construct by a pump such as a mechanical pump. The biological fluid is one that can readily move through the lumen of the matrix. Example fluids include. but are not limited to, culture medium. buffer medium, and physiological medium. The composition and viscosity of the biological fluid can be altered to be the equivalent to blood. This can be accomplished by adding high molecular weight proteins such as 40% of 100 kDa dextran to the culture medium, buffer medium, and physiological medium.

The exterior matrix can also be treated with the biological fluid. Adding a volume of biological fluid to the matrix such that the outside surface of the tubular matrix is exposed to the biological fluid can do this. In one embodiment, the biological fluid used to treat the inside of the vessel is the same as the biological fluid used to treat the outside of the vessel. In another embodiment, the biological fluid used to treat the inside of the vessel is different from the biological fluid used to treat the outside of the vessel. For example, the inside of the matrix (lumen side) can be treated with a biological fluid that is optimal for endothelial cell growth and proliferation, while the outside of the matrix can be treated with a biological fluid that is optimal for smooth muscle cell growth and proliferation.

In some embodiments, the pore structure of the exterior of the matrix and acellular character of the construct promotes or can be used to direct smooth muscle cell infiltration into the constructs. The outer layer of the bilayer construct can incorporate various growth factors to stimulate or proliferate cell growth in these constructs. In some embodiments, such incorporated growth factors can include, for example, platelet derived growth factor-BB (PDGF-BB) and/or stromal cell-derived factor 1-α (SDF-1α), which has been shown to act as a chemotactic agent that causes smooth muscle cells to proliferate and migrate to such regions. Both of these growth factors can also be incorporated in the polymer solution prior to the step of electrospinning. In some embodiments, the heparinized PCL/collagen scaffold can be prepared as described above. The PDGF-BB and/or SDF-1α can be bound to the heparinized scaffolds via electrostatic interactions. PDGF-BB and/or SDF-1α bound to the heparinized scaffolds can cause host smooth muscle cells to mobilize to the implanted scaffold.

BRIEF DESCRIPTION OF THE DRAWINGS

FIG. 18 at panel (A) shows a control with no additional growth factor added. FIG. 18 at panel (B) shows the resultant cell recruitment in the outer layer when stromal cell-derived factor 1-α (SDF-1α) was added to the solution prior to electrospinning. FIG. 18 at panel (C) shows the resultant cell recruitment in the outer layer when platelet derived growth factor-BB (PDGF-BB) was added to the solution prior to electrospinning. FIG. 18 at panel (D) shows the resultant cell recruitment in the outer layer when stromal cell-derived factor 1-α and platelet derived growth factor-BB were added to the solution prior to electrospinning.

DETAILED DESCRIPTION

Figure 1:
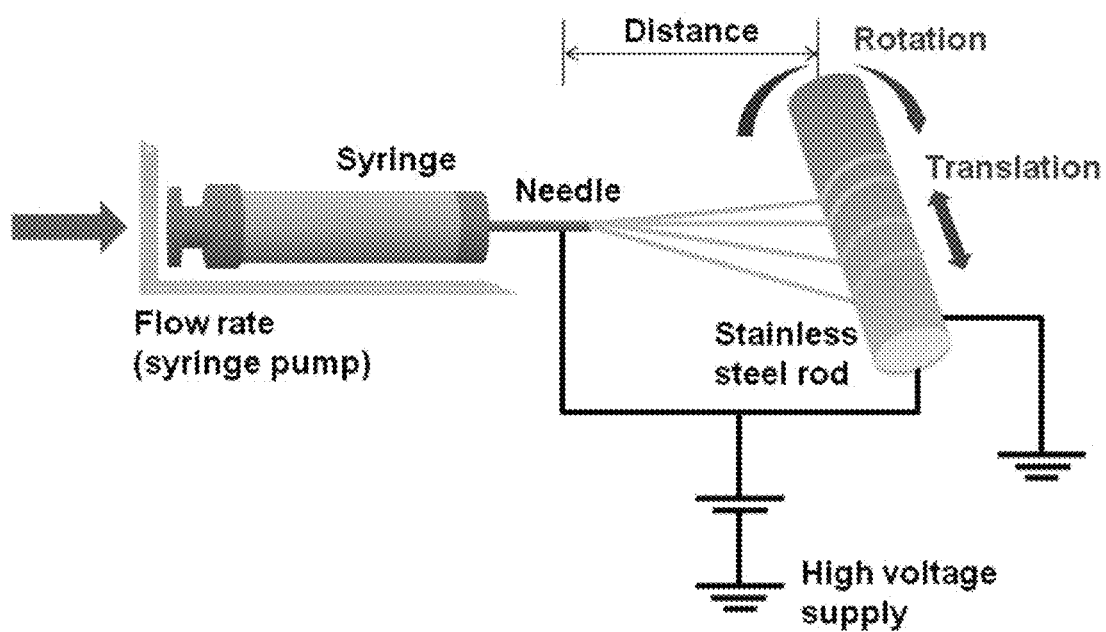
FIG. 1 is a schematic of an electrospinning apparatus.

So that the invention may more readily be understood, certain terms are first defined:

The terms "attach" or "attaches" as used herein refer to cells that adhere directly or indirectly to a substrate as well as to cells that adhere to other cells.

Biocompatible refers to materials that do not have toxic or injurious effects on biological functions. Biodegradable refers to material that can be absorbed or degraded in a patient's body. The phrase "biocompatible substrate" as used herein refers to a material that is suitable for implantation into a subject onto which a cell population can be deposited. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate provides the supportive framework that allows cells to attach to it, and grow on it. Cells can be attracted to and/or grown onto the biocompatible substrate, which provides the appropriate interstitial distances required for cell-cell interaction.

The term "bi-layer" as used herein in connection with electrospun matrices refers to matrices has two or more layers of different composition, typically different fiber sizes and different porosities.

The term "biological fluid" as used herein refers to a liquid that can be used to precondition an engineered blood vessel. The biological fluid can have a composition and viscosity that mimics blood so that the engineered blood vessels are exposed to the same fluid flow dynamics as native blood vessels. Examples of biological fluids can include any buffer, medium of physiological fluid (e.g., DMEM with 10% FCS with a blood viscosity). The viscosity of the fluids can be altered by adding high molecular weight proteins such as 100 kDa dextran. Other molecular weight dextrans can also be used. It will be appreciated that the amount of dextran to be used depends on the molecular weight and can range from about 10%, 20%, 30%, 40%, 50%, and 60%. The composition may also be varied by adding other blood like constituents such as salts.

The term "co-polymer" as used herein is intended to encompass co-polymers, ter-polymers, and higher order multiple polymer compositions formed by block, graph or random combination of polymeric components.

The term "decellularized" or "decellularization" as used herein refers to a biostructure (e.g., a vessel, an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures can be rigid, or semi-rigid, having an ability to alter their shapes. Examples of decellularized organs useful in the present invention include, but are not limited to, blood vessels, heart, kidney, liver, pancreas, spleen, bladder, ureter and urethra.

The terms "electrospinning" or "electrospun," as used herein refer to any method where materials are streamed, sprayed, sputtered, dripped, or otherwise transported in the presence of an electric field. The electrospun material can be deposited from the direction of a charged container towards a grounded target. or from a grounded container in the direction of a charged target. In particular, the term "electrospinning" means a process in which fibers are formed from a charged solution comprising at least one natural biological material. at least one synthetic polymer material, or a combination thereof by streaming the electrically charged solution through an opening or orifice towards a grounded target.

The terms "solution" as used in the context of producing an electrospun matrix describes a liquid that is capable of being charged and which comprises at least one natural material, at least one synthetic material, or a combination thereof. In a preferred embodiment, the fluid comprises at least one type of collagen or elastin, and at least one synthetic polymer, e.g., poly(ε-caprolactone) (PCL), poly(lactic acid) (PLA), or poly(lactide-co-glycolide) (PLGA).

The terms "nanoparticles," "nanostructures," and "quantum dots" are used interchangeably herein to describe materials having dimensions of the order of one or a few nanometers to a few micrometers, more preferably from about 1 to about 1,000 nanometers.

A "natural biological material" can be a naturally occurring organic material including any material naturally found in the body of a mammal, plant, or other organism. A "synthetic polymer material" can be any material prepared through a method of artificial synthesis, processing, or manufacture. Preferably the synthetic materials are biologically compatible materials. The natural or synthetic materials are also those that are capable of being charged under an electric field.

The term "natural biostructure" as used herein refers to a biological arrangement found within a subject, for example, organs, that include but are not limited, blood vessels, heart, kidney, liver, pancreas, spleen, bladder, ureter and urethra. The term "natural biostructure" is also intended to include parts of biostructures, for example parts of organs, for example. the renal artery of a kidney.

The term "pore size" is typically described in terms of the distance between adjacent fibers as observed by microscopy. The term "pore area" is likewise measurable by microscopy and typically reported in square microns.

The term "preconditioning chamber" as used herein refers to a container that allows a matrix to develop under physiological conditions. For example, to create blood vessels, a matrix is pulsed under conditions that mimic the pulse rate of blood through native vessels, or fluid flow conditions with alterations in pressure. To begin with, the pulse rate and the flow rate can be slow and pulse-rate can then gradually be increased. By gradually increasing the pulse-rate and the flow-rate, the vessels become conditioned to being able to withstand pressure as high as those produced during each heartbeat. The biological fluid can be moved through the inside surface of the attached matrix (lumen) as a continuous flow, for example at a flow-rate that can be incremented over time to induce a wall shear in the range of about 1 dyne/cm$^2$ to about 30 dynes/cm$^2$. The step of preconditioning the matrix can also involve moving the biological fluid through the inside surface of the attached matrix as a pulsed flow, for example, a pulsed flow that has a pulse-rate which is incremented over time to induce a wall shear in the range of about 10 dynes/cm$^2$ to about 45 dynes/cm$^2$. The pulse-rate can be incremented over time to induce a wall pressure distribution in the engineered blood vessel in the range of about 60 to about 200 mmHg. A different or the same biological fluid can also be used to precondition the outside of the matrix.

The terms "treat" or "treating" is used herein to include the method used to coat a surface, including the internal lumen or external surface of a tubular matrix, with therapeutic agents including: factors, including nutrients, growth factors, inducers of differentiation or dedifferentiation. EC/EPC-specific antibodies, products of secretion, immunomodulators, inhibitors of inflammation, regression factors, biologically active compounds which enhance or allow ingrowth of the lymphatic network or nerve fibers, and drugs, such as anti-thrombogenic agents (i.e. heparin).

The term "coating" refers to conjugating or permeating a matrix with a material. Coating may be performed in one layer, or multiple layers until the desired properties are achieved. "Conjugating" may be performed in a manner known in the art to covalently bind the compound or compounds to the components of the matrices. "Activation" refers to an initial treatment of a surface to assist or promote conjugation and may also be performed in a manner known in the art.

The term "subject" as used herein is intended to include living organisms. Preferred subjects are mammals. Examples of subjects include but are not limited to, humans, monkeys, dogs, cats, mice, rates, cows, horses, pigs, goats and sheep.

The phrase "three-dimensional ultrastructure" as used herein refers to the residual infra-structure formed when a natural biostructure, e.g. an organ or vessel, is decellularized or the matrix developed when electrospinning is used to produce a vascular construct. This complex, three-dimensional ultrastructure provides the supportive framework that allows cells to attach to it, and grow on it. Cells can grow on the three-dimensional ultrastructure, which provides the exact interstitial distances required for cell-cell interaction. This provides a reconstructed organ that resembles the native in vivo organ. This three-dimensional ultrastructure can be perfused with therapeutic agents or a population of cultured cells, e.g., endothelial cells, which grow and develop to provide an endothelial tissue layer capable of supporting growth and development of at least one additional cultured cell population.

The constructs can be characterized for mechanical properties such as tensile strength using an Instron tester, for polymer molecular weight by gel permeation chromatography (GPC), glass transition temperature by differential scanning calorimetry (DSC) and bond structure by infrared (IR) spectroscopy; with respect to toxicology by initial screening tests involving Ames assays and in vitro teratogenicity assays, and implantation studies in animals for immunogenicity, inflammation, release and degradation studies. In vitro cell attachment and viability can be assessed using scanning electron microscopy, histology. and quantitative assessment with radioisotopes.

Electrospun Matrices

In some embodiments, the self-seeding vascular graft is an electrospun matrix having a tubular shape with an outside surface and a lumen that defines an inside surface and a three-dimensional ultrastructure of interconnected fibers with pores, wherein one or more EPC-specific antibodies and one or more anti-thrombogenic agents are conjugated to the lumen.

In certain embodiments, the interconnected fibers have varying fiber size. In embodiments described herein, the fiber size, measured as diameter size, can be from about 0.01 micron to about 10 microns, from about 0.1 micron to about 5 microns, or from about 1 micron to about 2.5 microns. In some embodiments, the fiber diameter is about 0.27 micron, about 1.00 micron, about 2.39 microns, or about 4.45 microns. Without wishing to be bound by theory, an increase in fiber diameter of the interconnected fibers increases the pore size of the three-dimensional ultrastructure. The larger pore size encourages attachment of smooth muscle cells to the matrix and the smaller pore size encourages the attachment of endothelial cells.

In some embodiments, the three-dimensional ultrastructure of interconnected fibers forms a bilayer each having different pore sizes. In certain embodiments, the inner layer has a smaller pore size than the pore size of the outer layer. In certain embodiments, the outer layer has a smaller pore size than the pore size of the inner layer. In certain embodiments, the inner layer average pore size is from about 0.01 micron to about 3 microns, from about 0.1 micron to about 2 micron, or from about 0.3 micron to about 0.5 micron. In certain embodiments, the outer layer pore size is from about 1 micron to about 5 microns, from about 2.5 microns to about 4.5 microns, or from about 3 microns to about 4 microns.

The process of electrospinning generally involves the creation of an electrical field at the surface of a liquid. The resulting electrical forces create a jet of liquid which carries electrical charge. The liquid jets may be attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening): or by a curing mechanism (chemically induced hardening). The produced fibers are collected on a suitably located, oppositely charged target substrate. For blood vessel constructs, the target substrate is preferably a spinning mandrel.

The electrospinning apparatus includes an electrodepositing mechanism and a target substrate. The electrodepositing mechanism includes at least one container to hold the solution that is to be electrospun. The container has at least one orifice or nozzle to allow the streaming of the solution from the container. If there are multiple containers, a plurality of nozzles may be used. One or more pumps (e.g., a syringe pump) used in connection with the container can be used to control the flow of solution streaming from the container through the nozzle. The pump can be programmed to increase or decrease the flow at different points during electrospinning.

The electrospinning occurs due to the presence of a charge in either the orifices or the target, while the other is grounded. In some embodiments, the nozzle or orifice is charged and the target is grounded. Those of skill in the electrospinning arts will recognize that the nozzle and solution can be grounded and the target can be electrically charged.

The target can also be specifically charged or grounded along a preselected pattern so that the solution streamed from the orifice is directed into specific directions. The electric field can be controlled by a microprocessor to create an electrospun matrix having a desired geometry. The target and the nozzle or nozzles can be engineered to be movable with respect to each other thereby allowing additional control over the geometry of the electrospun matrix to be formed. The entire process can be controlled by a microprocessor that is programmed with specific parameters that will obtain a specific preselected electrospun matrix.

In embodiments in which two materials combine to form a third material, the solutions containing these components can be mixed together immediately before they are streamed from an orifice in the electrospinning procedure. In this way, the third material forms literally as the microfibers in the electrospinning process. While the following is a description of a preferred method, other protocols can be followed to achieve the same result.

In FIG. 1, a syringe or micropipette, with an orifice, nozzle, or needle, is filled with a solution with at least one natural material, and at least one synthetic material. The syringe is suspended opposite a grounded target, such as a metal ground screen. A fine wire 18 is placed in the solution to charge the solution in the container to a high voltage. At a specific voltage determined for each solution, the solution in the needle is directed towards the grounded target. The single jet stream of materials forms a splayed jet, upon reaching the grounded target, e.g., a rapidly rotating mandrel. The splayed jet collects and dries to form a three-dimensional, ultra-thin, interconnected matrix of electrospun fibers. In some embodiments, a plurality of syringes can be used with each holding a different compound or solution.

Minimal electrical current is involved in the electrospinning process, therefore the process does not denature the materials that form the electrospun matrix, because the current causes little or no temperature increase in the solutions during the procedure.

The electrospinning process can be manipulated to meet the specific requirements for any given application of the electrospun matrix. In one embodiment, a syringe can be mounted on a frame that moves in the x, y and z planes with respect to the grounded substrate. In another embodiment, a syringe can be mounted around a grounded substrate, for instance a tubular mandrel. In this way. the materials that form the matrix streamed from a syringe can be specifically aimed or patterned. Although the micropipette can be moved manually, the frame onto which the syringe is mounted can also be controlled by a microprocessor and a motor that allows the pattern of streaming to be predetermined. Such microprocessors and motors are known to one of ordinary skill in the art, for example matrix fibers can be oriented in a specific direction, they can be layered, or they can be programmed to be completely random and not oriented.

In some embodiments, the electrospinning process is used to produce a bi-layered scaffold. The primary electrospinning provides a small fiber diameter and the secondary electrospinning provides a large fiber diameter. Not wishing to be bound by theory, the small fiber diameter allows for EC adhesion and the large fiber diameter allows for SMC infiltration.

Figure 2:
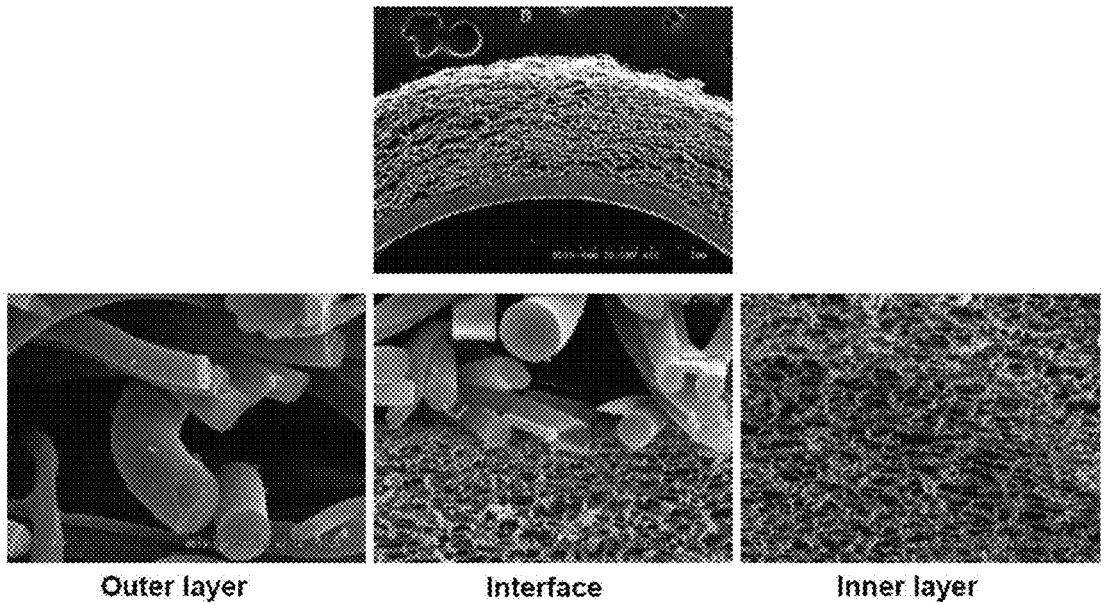
FIG. 2 shows SEM images of a bilayered vascular scaffold. Top image shows a portion of the bilayered vascular scaffold. The bottom middle image shows the interface of the two layers. The bottom left image is the outer layer and the bottom right image is the inner layer.

FIG. 2 provides images of the bi-layered scaffold. The top image in FIG. 2 shows a portion of the bilayered vascular scaffold. The bottom middle image shows the interface of the two layers. The bottom left image is the outer layer and the bottom right image is the inner layer.

Figures 3A, 3B, 3C:
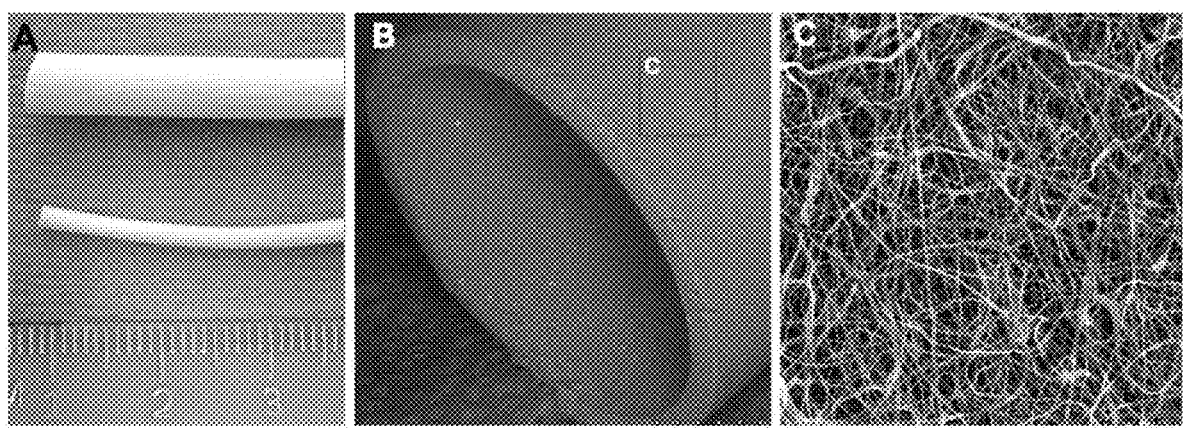
FIG. 3A is an image of 2 different-sized electrospun nanofibers.
FIG. 3B is an SEM image of electrospun nanofiber of FIG. 3A.
FIG. 3C is an image showing the texture of the electrospun fibers.

FIG. 3A is an image of 2 different-sized electrospun nanofiber constructs. FIG. 3B is an SEM image of electrospun nanofiber of FIG. 3A. FIG. 3C is an image showing the texture of the electrospun fibers.

Figure 4A:
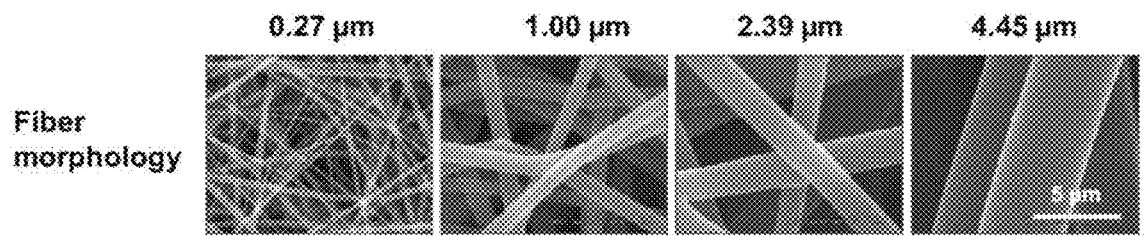
FIG. 4A presents SEM images depicting the fiber morphology of PCL/collagen vascular scaffolds with four different fiber diameters.
Figure 4B:
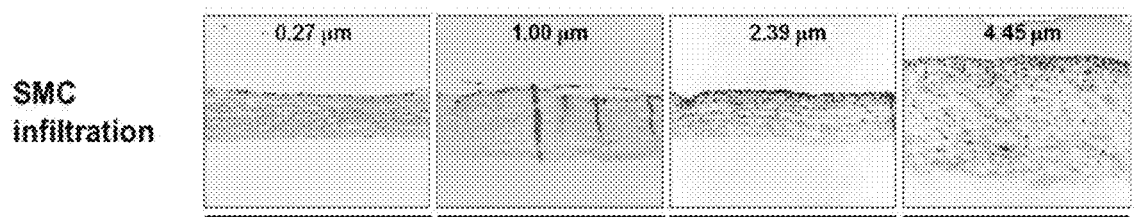
FIG. 4B are DAPI staining images demonstrating the SMC infiltration into each of the scaffolds (×100).
Figure 4C:
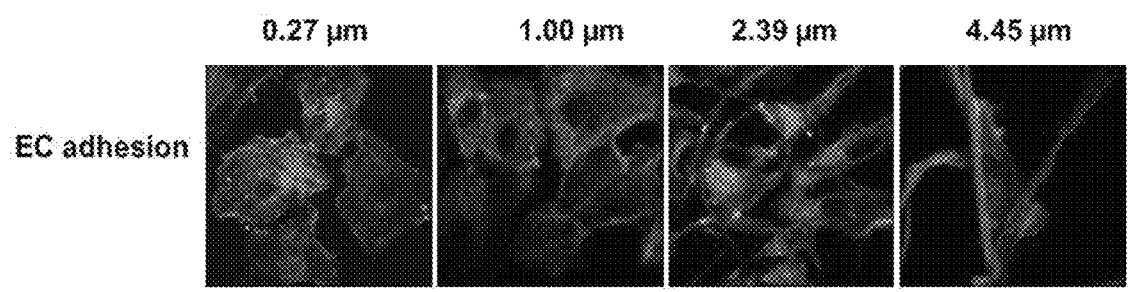
FIG. 4C shows the cytoskeletal organization and focal adhesion of ECs on each of the scaffolds after 12 hours of culture.

FIG. 4A provides fiber morphologies images using SEM of PCL/collagen vascular scaffolds with four different fiber diameters (0.27 µm, 1 µm, 2.39 µm, and 4.45 µm). FIG. 4B are DAPI staining of SMC infiltration into scaffolds (×100) of each of the four fiber diameters. FIG. 4C shows the cytoskeletal organization and focal adhesion of ECs on each of the four diameter scaffolds after 12 hours of culture.

The degree of branching can be varied by many factors including, but not limited to, voltage (for example ranging from about 0 to 30,000 volts), distance from a syringe tip to the substrate (for example from 1-100 cm, 0-40 cm, and 1-10 cm), the speed of rotation, the shape of the mandrel, the relative position of the a syringe tip and target (i.e. in front of, above, below, aside etc.), and the diameter of a syringe tip (approximately 0-2 mm), and the concentration and ratios of compounds that form the electrospun matrix. Other parameters which are important include those affecting evaporation of solvents such as temperature, pressure, humidity. The molecular weight of the polymer improves its ability to entangle and form fibers, and polymers with the molecular weight of 100 kDa generally performed. Those skilled in the art will recognize that these and other parameters can be varied to form electrospun materials with characteristics that are particularly adapted for specific applications. Preferred parameters can be found in Table 1.

TABLE 1

Fabrication parameters of electrospun PCL/
collagen scaffolds with various fiber diameters.

| | Polymer solution | | | Electrospinning device | | | |
|---|---|---|---|---|---|---|---|
| Fabrication Conditions | PCL/collagen (1:1) amount (mg) | Solution concentration (w/v %) | Solution volume (ml) | Flow rate (ml/h) | Needle gauge (G) | Distance (cm) | Voltage (kV) |
| FC1 | 225 | 5 | 4.5 | 3 | 18 | 10 | 25 |
| FC2 | 450 | 10 | 4.5 | 3 | 18 | 10 | 25 |
| FC3 | 450 | 15 | 3 | 3 | 18 | 10 | 25 |
| FC4 | 450 | 15 | 3 | 10 | 16 | 20 | 25 |

Fabrication Condition FC1 yielded fibers having an average diameter of about 500 nanometers (0.5 micrometers). Fabrication Condition FC2 yielded fibers having an average diameter of about 1 micrometers. Fabrication Condition FC3 yielded fibers having an average diameter of about 2 micrometers. Fabrication Condition FC4 yielded fibers having an average diameter of about 5 micrometers.

The geometry of the grounded target can be modified to produce a desired matrix. By varying the ground geometry, for instance having a planar or linear or multiple points ground, the direction of the streaming materials can be varied and customized to a particular application. For instance, a grounded target comprising a series of parallel lines can be used to orient electrospun materials in a specific direction. The grounded target can be a cylindrical mandrel whereby a tubular matrix is formed. The ground can be variable surface that can be controlled by a microprocessor that dictates a specific ground geometry that is programmed into it. Alternatively, the ground can be mounted on a frame that moves in the x, y, and z planes with respect to a stationary container, e.g., a syringe or micropipette tip.

Electrospinning allows great flexibility and allows for customizing the construct to virtually any shape needed. In shaping matrices, portions of the matrix may be sealed to one another by, for example. heat sealing, chemical sealing, and application of mechanical pressure or a combination thereof. The electrospun compositions may be shaped into shapes such as a skin patch, an intraperitoneal implant, a subdermal implant, the interior lining of a stent, a vessel, a cardiovascular valve, a tendon. a ligament, a muscle implant, a nerve guide and the like.

The electrospinning process can also be modified for example by (i) using mixed solutions (for example, materials along with substances such as cells, growth factors, or both) in the same container to produce fibers composed of electrospun compounds as well as one or more substances to produce a "blend," and (ii) applying agents such as Teflon onto the target to facilitate the removal of electrospun compounds from the target (i.e., make the matrix more slippery so that the electrospun matrix does not stick to the target).

The various properties of the electrospun materials can be adjusted in accordance with the needs and specifications of the cells to be grown within them. The porosity, for instance, can be varied in accordance with the method of making the electrospun materials or matrix. Electrospinning a particular matrix, for instance, can be varied by fiber size and density. If the cells to be grown in the matrix require a high nutrient flow and waste expulsion, then a loose matrix can be created. On the other hand, if the tissue to be made requires a dense environment, then a dense matrix can be designed. Porosity can be manipulated by mixing salts or other extractable agents. Removing the salt will leave holes of defined sizes in the matrix.

For electrospinning matrices according to the invention, approximate ranges for various parameters of the process can be as follows: voltage 0-30.000 volts (10-100 kV potential preferably 15-30 kV); pH 7.0 to 8.0; temperature 20 to 40° C., e.g., room temperature of 25° C.; and the distance from the container to the grounded plate can range from about 1 cm to about 100 cm, preferably about 1 cm to 10 cm. In addition to depositing the charged fibers on the grounded plate, the fibers can be deposited onto another substrate such as a stainless steel mandrel. The mandrel can be rotated at 20-1000 rpm, preferably about 300-700 rpm.

Examples of naturally occurring materials that can form or be incorporated into electrospun matrices include, but are not limited to, amino acids, peptides, denatured peptides such as gelatin from denatured collagen, polypeptides, proteins, carbohydrates. lipids, nucleic acids, glycoproteins, lipoproteins, glycolipids, glycosaminoglycans, and proteoglycans. In a preferred embodiment, the materials compound is an extracellular matrix material, including but not limited to chondroitin 4-sulfate, chondroitin 6-sulfate, collagen, dermatan sulfate, elastin, fibrin. fibronectin, gelatin, heparin, heparin sulfate, hyaluronic acid, keratan sulfate, laminin, and proteoglycans. These materials may be isolated from humans or other animals or cells.

A preferred natural compound is collagen. Examples of collagen include, but are not limited to collagen I, collagen II. collagen III, collagen IV, collagen V, collagen VI, collagen VII, collagen VIII, collagen IX, and collagen X. Another preferred natural compound is elastin. Elastin fibers are responsible for the elastic properties of several tissues. Elastin is found, for example, in skin, blood vessels, and tissues of the lung where it imparts strength, elasticity and flexibility.

One class of synthetic polymer materials are biocompatible synthetic polymers. Such polymers include, but are not limited to, polycaprolactone (PCL), poly(lactic acid) (PLA), poly(glycolic acid) (PGA), poly(lactide-co-glycolide)s (PL-GAs). poly(lactide-co-ε-caprolactone)s (PLCL)s, poly(urethanes), poly(siloxanes) or silicones, poly(ethylene), poly (vinyl pyrrolidone), poly(2-hydroxy ethyl methacrylate), poly(N-vinyl pyrrolidone), poly(methyl methacrylate). poly (vinyl alcohol) (PVA), poly(acrylic acid). poly(vinyl acetate). polyacrylamide, poly(ethylene-co-vinyl acetate), poly(ethylene glycol), poly(methacrylic acid), nylons, polyamides, polyanhydrides, poly(ethylene-co-vinyl alcohol) (EVOH), poly(vinyl acetate), poly(vinyl hydroxide), poly (ethylene oxide) (PEO) and polyorthoesters or any other similar synthetic polymers that may be developed that are biologically compatible. Preferred synthetic polymers include PCL and PLGA.

In matrices composed of electrospun collagen (to promote cell infiltration and lend mechanical integrity), and other components, such as PCL, PLGA. PGA, PLA, PLCL, PEO, PVA, or other blends, and, optionally elastin (for elasticity), the relative ratio of the different components in the matrix can be tailored to specific applications (e.g. more PCL, less collagen depending on the tissue to be engineered).

Electrospun matrices can be formed of electrospun fibers of synthetic polymers that are biologically compatible. The term "biologically compatible" includes copolymers and blends, and any other combinations of the forgoing either together or with other polymers. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated herein by reference.

When both natural and synthetic materials are used in an electrospun matrix, the natural material component can range from about 5 percent to about 95 percent, preferably from about 25 percent to about 75 percent by weight. The synthetic material component can range from about 5 percent to about 95 percent, preferably from about 25 percent to about 75 percent by weight. In certain embodiments, both collagen and elastin can be included as natural material components, preferably with a predominance of collagen, e.g., greater than 40 percent of the natural material component. Ratios of collagen and PCL and optional tertiary materials may be tailored to fit the application: for instances, normal levels of collagen and elastin vary from the more elastic vessels closer to the heart to less compliant vessels further from the heart. A vessel such as the aorta may include elastin or have a greater elastin content than a distal vessel. The percentages of collagen I, elastin, and/or other collagens may be whatever is desired, as long as the molecular weight of these components is sufficient to form fibers in the electrospinning process. The weight percentage of collagen may range from about 40% to about 80%. Elastin may also be present by weight percentage of from about 0% to about 50%. PCL. PLGA or another synthetic biodegradable polymer may be used as desired in ratios from about 5% to about 80%. For a completely biological substrate, synthetic polymers may be omitted completely and only biological polymers may be used.

The compounds to be electrospun can be present in the solution at any concentration that will allow electrospinning. In one embodiment, the compounds may be electrospun are present in the solution at concentrations between 0 and about 1.000 g/ml. In another embodiment, the compounds to be electrospun are present in the solution at total solution concentrations between about 10-15 w/v % (100-150 mg/ml or 0-0.1 g/L).

The compounds can be dissolved in any solvent that allows delivery of the compound to the orifice, tip of a syringe, under conditions that the compound is electrospun. Solvents useful for dissolving or suspending a material or a substance will depend on the compound. Electrospinning techniques often require more specific solvent conditions. For example, fiber materials can be electrodeposited as a solution or suspension in water, 2,2,2-trifluoroethanol, 1,1,1,3,3,3-hexafluoro-2-propanol (also known as hexafluoroisopropanol or HFIP), or combinations thereof. Fibrin monomer can be electrodeposited or electrospun from solvents such as urea, monochloroacetic acid, water, isopropanol, 2,2,2-trifluoroethanol, HFIP. or combinations thereof. Other lower order alcohols, especially halogenated alcohols, may be used. Other solvents that may be used or combined with other solvents in electrospinning natural matrix materials include acetamide, N-methylformamide, N,N-dimethylformamide (DMF), dimethylsulfoxide (DMSO), dimethylacetamide, N-methyl pyrrolidone (NMP), acetic acid. trifluoroacetic acid, ethyl acetate, acetonitrile, trifluoroacetic anhydride, 1,1,1-trifluoroacetone, maleic acid, hexafluoroacetone. Other organic solvents such as methanol, chloroform, and trifluoroethanol (TFE) and emulsifying agents may also be added.

The selection of a solvent is based in part on consideration of secondary forces that stabilize polymer-polymer interactions and the solvent's ability to replace these with strong polymer-solvent interactions. In the case of polypeptides such as collagen. and in the absence of covalent crosslinking, the principal secondary forces between chains are: (1) coulombic, resulting from attraction of fixed charges on the backbone and dictated by the primary structure (e.g., lysine and arginine residues will be positively charged at physiological pH, while aspartic or glutamic acid residues will be negatively charged); (2) dipole-dipole. resulting from interactions of permanent dipoles; the hydrogen bond, commonly found in polypeptides, is the strongest of such interactions; and (3) hydrophobic interactions, resulting from association of non-polar regions of the polypeptide due to a low tendency of non-polar species to interact favorably with polar water molecules. Therefore, solvents or solvent combinations that can favorably compete for these interactions can dissolve or disperse polypeptides. For example, HFIP and TFE possess a highly polar OH bond adjacent to a very hydrophobic fluorinated region. While not wanting to be bound by the following theories, it is believed that the alcohol portion can hydrogen bond with peptides, and can also solvate charges on the backbone, thus reducing Coulombic interactions between molecules. Additionally, the hydrophobic portions of these solvents can interact with hydrophobic domains in polypeptides. helping to resist the tendency of the latter to aggregate via hydrophobic interactions. It is further believed that solvents such as HFIP and TFE, due to their lower overall polarities compared to water, do not compete well for intramolecular hydrogen bonds that stabilize secondary structures such as an alpha helix. Consequently. alpha helices in these solvents are believed to be stabilized by virtue of stronger intramolecular hydrogen bonds. The stabilization of polypeptide secondary structures in these solvents is believed desirable, especially in the cases of collagen and elastin, to preserve the proper formation of collagen fibrils during electrospinning.

In one embodiment, the solvent has a relatively high vapor pressure to promote the stabilization of an electrospinning jet to create a fiber as the solvent evaporates. In embodiments involving higher boiling point solvents, it is often desirable to facilitate solvent evaporation by warming the spinning or spraying solution, and optionally the electrospinning stream itself, or by electrospinning in reduced atmospheric pressure. It is also believed that creation of a stable jet resulting in a fiber is facilitated by a high surface tension of the polymer/solvent mixture.

Similar to conventional electrospinning, midair electrospinning can be used which employs the same experimental set-up as other electrospinning techniques. However, in order to precipitate fibers before they reach the grounded target. the distance from the needle to the grounded target can be increased. For example, increasing the distance from the 10-30 cm to a distance of 30-40 cm. The field strength can be maintained or altered by increasing the applied potential at the needle tip. Increasing the distance from the needle tip to the grounded target allows the polymer jet to experience a longer "flight time." The added flight time, allows the solvent to be completely evaporated from the jet allowing the fibers to fully develop.

By varying the composition of the fibers being electrospun, it will be appreciated that fibers having different physical or chemical properties may be obtained. This can be accomplished either by spinning a liquid containing a plurality of components, each of which may contribute a desired characteristic to the finished product, or by simultaneously spinning fibers of different compositions from multiple liquid sources, that are then simultaneously deposited to form a matrix. The resulting matrix comprises layers of intermingled fibers of different compounds. This plurality of layers of different materials can convey a desired characteristic to the resulting composite matrix with each different layer providing a different property, for example one layer may contribute to elasticity while another layer contributes to the mechanical strength of the composite matrix. These methods can be used to create bilayered scaffolds or tissues with multiple layers such as blood vessels.

The electrospun matrix has an ultrastructure with a three-dimensional network that supports cell growth, proliferation, differentiation and development. The spatial distance between the fibers plays an important role in cells being able to obtain nutrients for growth as well as for allowing cell-cell interactions to occur. Thus, in various embodiments of the invention, the distance between the fibers (i.e. the average pore size) may be about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 10 microns, 10 microns, 50 microns, about 100 microns, about 150 microns, about 200 microns. about 250 microns, about 300 microns, about 350 microns, about 400 microns, about 450 microns, or about 500 microns. In various embodiments the distance between the fibers may be less than 50 nanometers or greater than 500 microns and any length between the quoted ranges as well as integers.

Additionally, in various embodiments of the invention, the fibers can have a diameter of about 50 nanometers. about 100 nanometers, about 150 nanometers, about 200 nanometers, about 250 nanometers, about 300 nanometers. about 350 nanometers, about 600 nanometers. about 750 nanometers, about 800 nanometers, about 850 nanometers. about 900 nanometers. about 950 nanometers, about 1000 nanometers (1 micron). 50 microns, about 100 microns, about 150 microns, about 200 microns, about 250 microns, about 300 microns, about 350 microns, about 400 microns, about 450 microns. or about 500 microns, or the diameter may be less than 50 nanometers or greater than 500 microns and any diameter between the quoted ranges as well as integers.

In one preferred embodiment, the bi-layered electrospun tubular matrices can have an outer region, in which the average fiber size is greater than 1 micron (e.g. between 1 and 10 microns or between 1 and 5 microns), and an inner region, in which average fiber size is less than 1 micron (e.g. between 100 and 900 nanometers, or between 200 and 700 nanometers).

The pore size in an electrospun matrix can also be controlled through manipulation of the composition of the material and the parameters of electrospinning. In some embodiments, the inner region of the electrospun tubular matrix has a pore size that is small enough to be impermeable to one or more types of cells and an outer region with pore sizes that do not substantially impede cell infiltration. For example, the bi-layered electrospun tubular matrices can have an inner region, in which the average pore size is less than 1 micron (e.g., between 100 and 900 nanometers, or between 200 and 700 nanometers) and an outer region, in which the average pore diameter is greater than 1 micron (e.g., between 1 micron and 10 microns or between 1 and 5 microns).

The pore area will also vary between the inner and outer regions of the bi-layered matrix. For example, the bi-layered electrospun tubular matrices can have an inner region, in which the average pore area is less than 100 $\mu m^2$ (e.g., between about 0.5 and about 50 $\mu m^2$) and an outer region in which the average pore area is greater than 100 $\mu m^2$ (e.g., between about 200 and about 2000 $m^2$).

The pore size (and pore area) of an electrospun matrix can be readily manipulated through control of process parameters, for example by controlling fiber deposition rate through electric field strength and mandrel motion, by varying solution concentration (and thus fiber size). Porosity can also be manipulated by mixing porogenic materials, such as salts or other extractable agents, the dissolution of which will leave holes of defined sizes in the matrix. The pore size can also be controlled by the amount of crosslinking present in the matrix.

The mechanical properties of the matrix will depend on the polymer molecular weight and polymer type/mixture. It will also depend on orientation of the fibers (preferential orientation can be obtained by changing speed of a rotating or translating surface during the fiber collection process), fiber diameter and entanglement. The crosslinking of the polymer will also effect its mechanical strength after the fabrication process.

The electrospun matrix can be crosslinked to increase its stability and strength. The crosslinking can generally be conducted at room temperature and neutral pH conditions; however, the conditions may be varied to optimize the particular application and crosslinking chemistry utilized. For crosslinking using the EDC chemistry with NHS in MES/EtOH, pH of from 4.0 to 8.0 and temperatures from 0° C. to room temperature (25° C.) for two hours, can be used. It is known that higher temperatures are unpreferred for this chemistry due to decomposition of EDC. Similarly, basic pH (e.g., 8-14) is also unpreferred for this reason when using this chemistry. Other crosslinking chemistries can also be used for example. by soaking the electrospun matrix in 20% dextran solution (to reduce shrinking), followed by 1% glutaraldehyde solution. Yet other crosslinking chemistries involve using poly(ethylene glycol) (PEG) as a spacer in a crosslinking agent with an N-protected amino acid.

Bioconjugation of Electrospun Matrices

Figure 5:
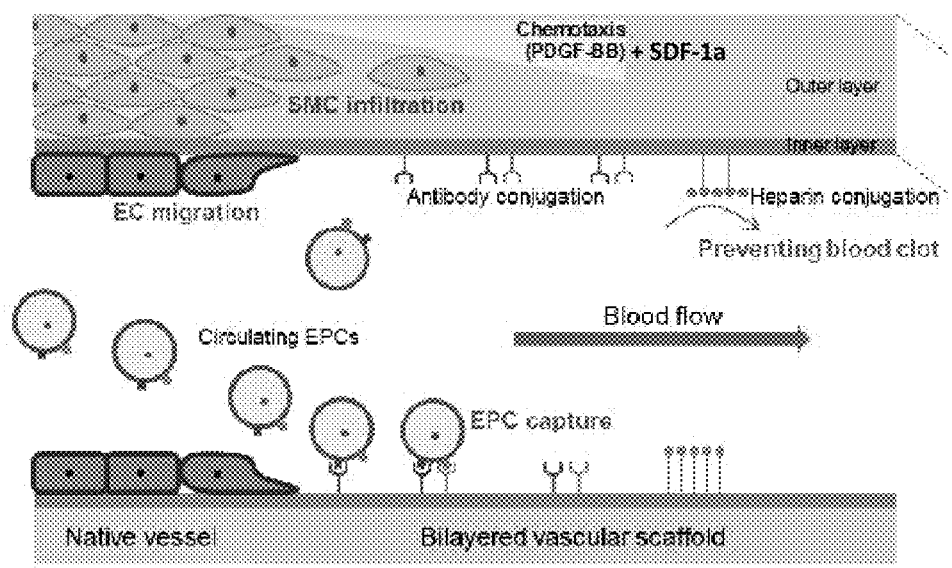
FIG. 5 depicts a schematic illustration of the antibody-enriched heparinized vascular scaffold in accordance with the invention in the process of self-assembly.

The concept of "in situ tissue regeneration," unlike cell-based tissue engineered blood vessels, is the use of self-seeding vascular constructs which utilize host biologic resources and microenvironment to create autologous vascular tissues. FIG. 5 shows how the functionalized self-seeding vascular graft can function in vivo: (i) Endothelial cells (ECs) migrate from the adjacent native vessel, and circulating EPCs adhere to the conjugated cell specific antibodies and captured on the luminal surface of the vascular graft, followed by differentiation into mature endothelial cells. (ii) Heparin conjugation provides the initial antithrombogenic effect.

The electrospun matrices, described herein, are treated with functional agents on the luminal surface to create bi-layered or multi-layered scaffolds conjugated with functional agents. Immobilization of endothelial progenitor cell (EPC)-specific antibodies (i.e. CD133) and one or more anti-thrombogenic agents (i.e. heparin) functions to prevent thrombosis and capture circulating EPCs that facilitate infiltration of host cells into the vascular graft. which eventually develops into mature vascular tissues in vivo.

Additional factors, including nutrients, growth factors, inducers of differentiation or dedifferentiation. products of secretion, immunomodulators, inhibitors of inflammation, regression factors, biologically active compounds which enhance or allow ingrowth of the lymphatic network or nerve fibers, and drugs can also be incorporated into the matrix or provided in conjunction with the matrix. In some embodiments, to enhance the attachment of the cells in vivo to the biocompatible substrate, the matrix can also be coated or conjugated with compounds such as basement membrane components, agar, agarose, gelatin, gum arabic, collagens, glycosaminoglycans, fibronectin, laminin, mixtures thereof, and other materials having properties similar to biological matrix molecules known to those skilled in the art of cell culture. Similarly, polymers containing peptides such as the attachment peptide RGD (Arg-Gly-Asp) can be applied to the matrices.

In some embodiments, EC/EPC-specific antibodies, such as CD133, CD31, CD34, CD45, CD146, CD202b, VE-cadherin, VEGF, Flk-1, and VEGFR3 are conjugated to the lumen of the vascular graft to promote in situ endothelialization. In some embodiments, heparin or other anti-thrombogenic agents are conjugated to the vascular graft to promote anti-thrombogenic effects. Preferably, the antibodies and/or heparin molecules are conjugated onto the vascular graft scaffolds using EDC (I-ethyl-3(3-dimethyl aminopropyl) carbodiimide) and NHS (N-hydroxyl-sulfo-succinimide) to form peptide bonds. For example, constructs can be activated by immersion in a 2-morpholinoethane sulfonic acid (MES) aqueous solution containing EDC and NHS for 30 min at 37° C. The antibodies and/or heparin can then be added to the reaction in a quantity sufficient to achieve the desired antibody and/or heparin concentration and incubated for 2 h at 37° C. The constructs can then be submerged in a termination buffer (e.g., ethanolamine and sodium chloride) for 1 h at room temperature. The functionalized constructs can then be washed by submerging in a washing buffer (e.g., trizma hydrochloride or a solution of sodium acetate trihydrate and sodium chloride) and then rinsed. The buffering and rinsing steps can be repeated as desired to ensure that the bioconjugated constructs are substantially free of any remaining reagents.

In certain embodiments, when antibodies and/or heparin molecules are conjugated onto the vascular graft scaffolds to form peptide bonds using EDC and NHS, the chemistry to form the EDC (1-ethyl-3(3-dimethyl aminopropyl) carbodiimide) and NHS (N-hydroxyl-sulfo-succinimide) peptide bonds is divided into a two-step process. In some embodiments, heparin can be first conjugated to electrospun vascular scaffold. The amount of heparin to be conjugated, for example, can be about 0.01-10 mg/mL. Following heparin conjugation. EC/EPC-specific antibodies can be conjugated onto the heparinized luminal surface. The amount of antibody to be conjugated, for example, can be about 1-1000 μg/mL.

Figure 6:
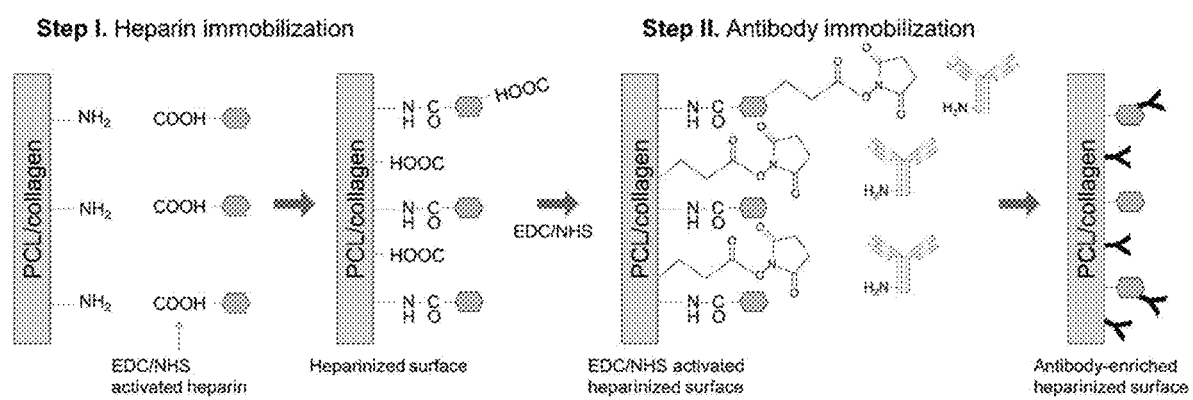
FIG. 6 depicts a schematic illustration of the functionalized surface for cell capture and in particular the stages of preparation. Step I, heparin immobilization, shows the carboxyl groups of the heparin molecules were activated using EDC/NHS. After the activation, the PCL/collagen surface was treated with EDC/NHS activated heparin molecules. Step II, antibody immobilization, shows the heparinized PCL/collagen surface was activated by using EDC/NHS for antibody conjugation.

FIG. 6 depicts a schematic illustration of the antibody-enriched heparinized vascular scaffold. In some embodiments, antibody conjugation can be improved by the heparinized surface due to the prevention of electrostatic repulsion. For example, following formation of the vascular scaffold, an antibody enriched and heparinized surface can facilitate capture and conjugation of circulating endothelial progenitor cells and/or permits migration of endothelial cells. Thickening of the vessel wall during cell recruitment can leads to graft stenosis and occlusion. Heparin can inhibit thickening of the vessel without limiting capture of circulating EPCs that eventually develop into mature vascular tissues in vivo.

Figure 7A:
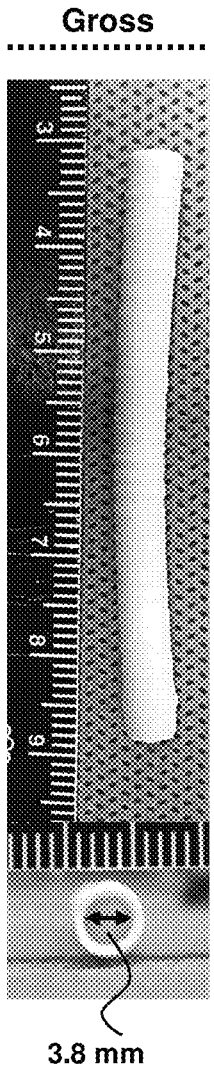
FIG. 7A shows images of an engineered vessel (i) along its length and (ii) across its diameter.
Figure 7B:
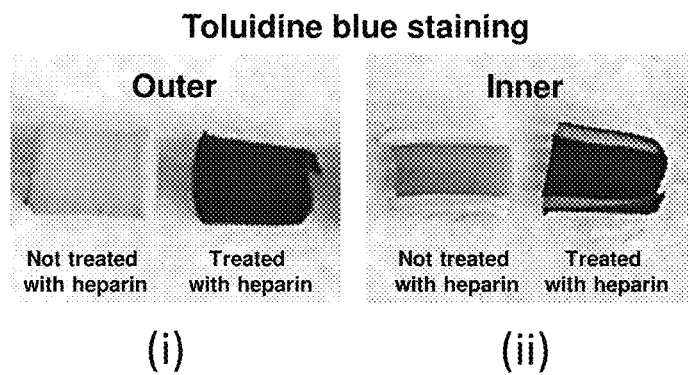
FIG. 7B shows images of the (i) outer surface of vessel and (ii) inner surface of vessel that were engineered with and without heparin conjugation. The vessels were stained with toluidine blue to show the heparin conjugation.
Figure 7C:
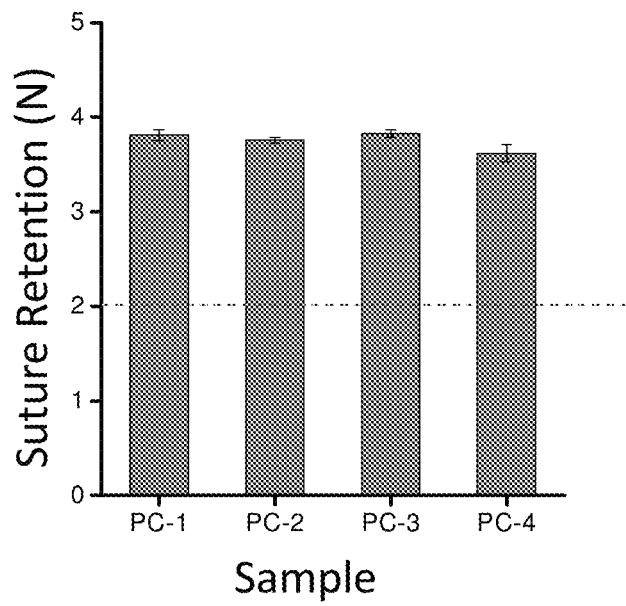
FIG. 7C depicts exemplary data showing the suture-holding capacity of a number of sample vessels, each similarly engineered with heparin conjugation.
Figure 8:
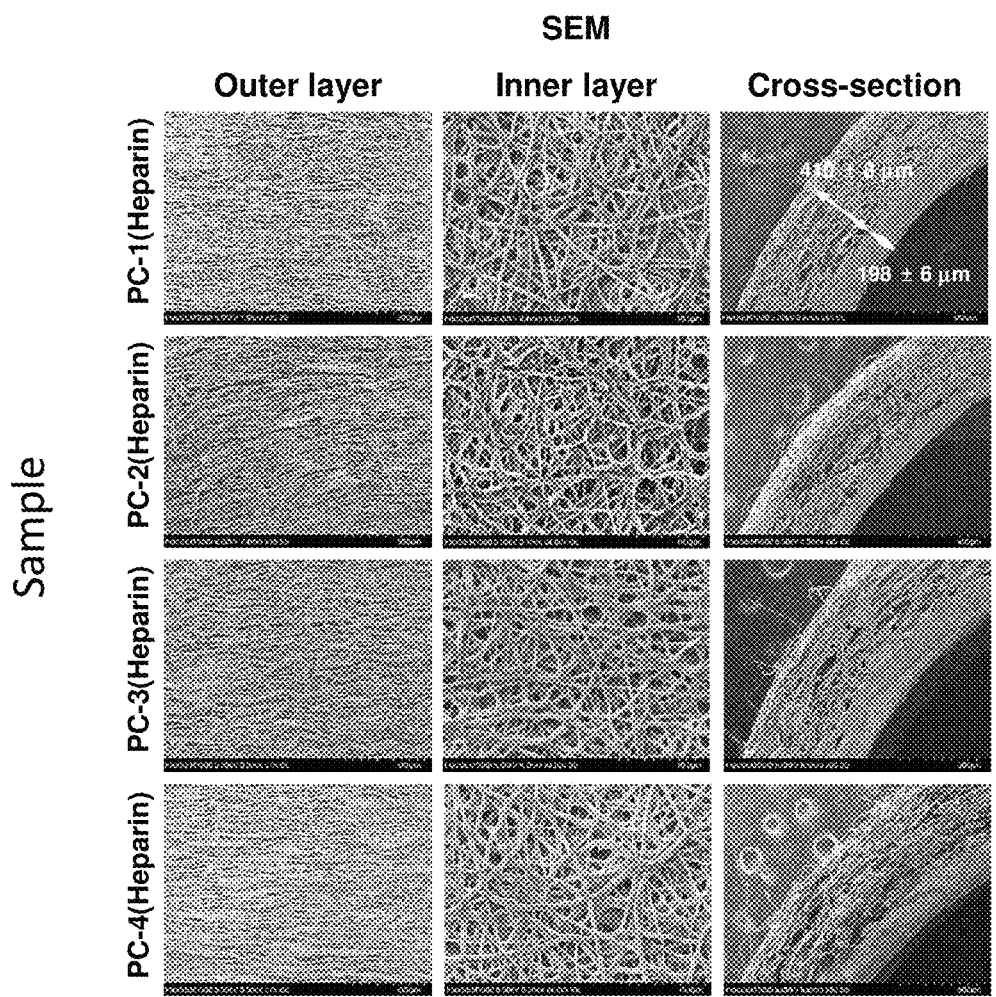
FIG. 8 shows SEM images of a bilayered vascular scaffolds. The vessel samples were similarly engineered with heparin conjugation. The left column of images shows the exterior layer of the bilayered vascular scaffold. The middle column of images shows the inner layer of the bilayered vascular scaffold. The right column of images shows an image of the bilayered vascular scaffolds wall showing the cross-section images of the outer and inner layer.

As described above, the electrospinning process can be used to produce a bi-layered scaffold. FIG. 7A provides images of an engineered scaffold. FIG. 7A at panel (i) shows a portion of a length of a bilayered vascular scaffold having a vessel-like appearance. The bottom image, FIG. 7A at panel (ii) shows a cross-section of an inner diameter of the scaffold. In this embodiment, the bilayered vascular scaffold has an inner diameter of about 3.8 mm, which certainly falls within the broad range of vessel diameters. FIG. 7B shows images of several bilayered vascular scaffolds stained with toluidine blue. The outer (i) and inner (ii) dark purple surfaces confirm heparin conjugation for the two right hand samples. FIG. 7C depicts exemplary data showing the suture-holding capacity of several bilayered vascular scaffolds, each similarly engineered via heparin conjugation. For comparison, each of the samples well exceeded the minimal acceptable suture-holding capacity for vessels, 2 (N), which is shown on the dotted line. FIG. 8 shows SEM images of these bilayered vascular scaffolds. The bilayered vascular scaffold samples PC-1 through PC-4 were similarly engineered with heparin conjugation and show uniformity.

In certain embodiments, more than one additive or drug can be conjugated to the vascular graft. For example, vascular endothelial growth factor (VEGF) can be employed to promote the formation of new vascular tissue. Growth factors and other additives (e.g., epidermal growth factor (EGF), heparin-binding epidermal-like growth factor (HBGF), fibroblast growth factor (FGF), cytokines. genes, proteins, and the like) can be added. Such additives are preferably provided in an amount sufficient to attract cells to the scaffold and promote the formation of new tissue of a type appropriate to the vascular structure that is to be repaired or augmented (e.g., by causing or accelerating infiltration of host cells into the graft). Other useful additives include antibacterial agents such as antibiotics. The material may be impregnated with suitable antimicrobial agents and may be colored by a color additive to improve visibility and to aid in surgical procedures.

The substrate or matrix can be fabricated to have a controlled pore structure that allows nutrients and cells from the culture medium to reach the deposited cell population. In vivo cell attachment and cell viability can be assessed using scanning electron microscopy, histology and quantitative assessment with radioisotopes. The substrate or matrix can be shaped into any number of desirable configurations to satisfy any number of overall system, geometry or space restrictions. It can also be shaped to different sizes to conform to the necessary structures of different sized patients.

The substrate can also be treated or seeded with various factors and proteins to control the degradation/absorption of the matrix in the subject. For instance, if the cells to self-seed within the substrate are slow-growing, then it is beneficial to maintain the matrix integrity for a long enough period of time to allow the cells enough time to regenerate and grow. On the other hand, if the cells are able to quickly reproduce and grow, then a short lived substrate can be desirable.

The constructs of the present invention can be further functionalized by incorporation of therapeutic, biological or imaging agents. For example, the electrospun matrix can also be functionalized to incorporate a contrast enhancing agent (e.g., gadolinium). Therapeutic or biological agents can be released in a controlled manner at a target site. For example, this can be accomplished using quantum dots to which the therapeutic/biological agent is coupled. Quantum dots are a semiconductor nanocrystal with size-dependent optical and electronic properties. In particular, the band gap energy of a quantum dot varies with the diameter of the crystal. The average diameter of the QDs may be between about 1 to about 100 nm, between about 10-80 nm, and between about 25-40 nm. The coupled agent can be released by application of energy such as near infrared (NIR) irradiation from a laser source, which causes the bonds between the agent and the QD to break and thus releases the agent. This allows the release of the agent to be controlled by triggering its release upon application of energy. Quantum dots have been used as photostable biological fluorescent tags, semiconductors, and thermal therapy. The high transmission, scattering-limited attenuation, and minimal heating effects of quantum dots makes these suitable for the coupling of therapeutic/biological agents. In one embodiment, NIR CdSe quantum dots (Evident Technologies) can be used. These QDs have an optical absorption range of 700-1000 nm. NIR energy within this spectral region has been shown to penetrate tissue at depths up to 23 cm with no observable damage to the intervening tissue.

A matrix functionalized with a QD coupled to a therapeutic or biological agent can be used for controlled release of the therapeutic or biological agent at a target in the subject. The therapeutic or biological agent can be released by application of energy at a desired wavelength such as near infrared irradiation. Due to localized heating of the QD, ultrastructural changes cause the release of the coupled agent. The release kinetics can be varied according to the type of QD used and the wavelength of irradiation. The release kinetics can also be varied by altering the intensity and time of irradiation. For example, a QD (e.g., CdSe QD from Evident Technologies) coupled to encapsulated heparin can be incorporated into an electrospun matrix. Upon application of near infrared radiation at a wavelength of 700-1000 nm, the heparin is released in a controlled manner, as described in the examples below. The therapeutic or biological agent can also be entrapped, for example encapsulated in a polymer with the QD. The encapsulated QD-agent can be mixed with a solution comprising at least one natural compounds, and at least one synthetic compound and electrospun into the matrix.

In particular, the therapeutic or biological agent and the nanoparticles (e.g., quantum dot) can be entrapped or encapsulated to produce "nanocapsules." These nanocapsules containing the agent and the nanoparticle can be produce standard encapsulating techniques. Microencapsulation of agents generally involves three steps: (a) generating microcapsules enclosing the agents (e.g., by forming droplets of cell-containing liquid alginate followed by exposure to a solution of calcium chloride to form a solid gel), (b) coating the resulting gelled spheres with additional outer coatings (e.g., outer coatings comprising polylysine and/or polyornithine) to form a semipermeable membrane; and (c) liquefying the original core gel (e.g., by chelation using a solution of sodium citrate). The three steps are typically separated by washings in normal saline.

In another aspect, the invention pertains to monitoring remodeling of tissue engineered vascular constructs. Remodeling that takes place too slowly can result in pathologic response of surrounding tissues and compliance mismatch of the vessel. Rapid remodeling can result in premature failure of the engineered construct. Magnetic Resonance Imaging (MRI) is a powerful. non-invasive technique that can be used long term for monitoring the remodeling process. Nanoparticles (e.g., QD, image enhancing agents) can be easily bound to electrospun matrices, and/or embedded within nanofibers of electrospun matrices. The nanoparticles provide high MRI contrast, and due to their small size, will not interfere with normal biological processes. Organolanthanide complexes containing paramagnetic metals such as gadolinium (Gd) have been known to cause distortion in an electromagnetic field. When the protons in water interact with this distorted field, their magnetic properties significantly change such that they can be detected by MRI. The Examples demonstrate the enhanced imaging observed using MRI contrast with Gd functionalized nanoparticles bound to the surface and/or incorporated into the vascular matrices or nanocapsules. Other examples of contrast enhancing agents include, but are not limited to, rare earth metals such as, cerium, samarium, terbium, erbium, lutetium. scandium, barium, bismuth, cerium, dysprosium, europium, hafnium, indium, lanthanum, neodymium, niobium, praseodymium, strontium, tantalum, ytterbium, yttrium, and zirconium.

In certain embodiments. the additional agents are joined to the matrix by peptide bonds in the same manner as the antibodies and/or heparin. For example, nanoparticles can be incorporated as part of the matrix using EDC (1-ethyl-3(3-dimethyl aminopropyl) carbodiimide) and sulfo-NHS (N-hydroxyl-sulfo-succinimide) to form peptide bonds.

Various other know techniques can be used to conjugate heparin, antibodies or other agents to the constructs of the present invention including techniques as described. for example, in Heumanson, Bioconjugate Techniques, Academic Press San Diego, Calif., 1996, herein incorporated by reference.

Various therapeutic and/or biological agents, including contrast enhancing agents, or agent-conjugated quantum dots can be added internally to an electrospun matrix by incorporating each component into the solution with at least one natural compound and at least one synthetic compound. For example, electrospinning solutions containing collagen and PCL can incorporate the contrast enhancing agent gadolinium. The incorporation of the gadolinium into the construct can be observed in vitro and in vivo using detection methods such as magnetic resonance imaging (MRI). Thus, a construct functionalized with a contrasting agent allows the degradation of the construct to be monitored.

Any type of functionalization method can be used. Examples of some possible functionalization chemistries include, but are not limited to, esterification (e.g., with acyl halides, acid anhydrides, carboxylic acids, or esters via interchange reactions), ether formation (for example, via the Williamson ether synthesis), urethane formation via reactions with isocyanates, sulfonation with, for example, chlorosulfonic acid, and reaction of b-sulfato-ethylsulfonyl aniline to afford an amine derivative that can be converted to a diazo for reaction with a wide variety of compounds. Such chemistries can be used to attach a wide variety of substances to the electrospun matrix, including but not limited to crown ethers (Kimura et al., (1983) J. Polym. Sci. 21, 2777), enzymes (Chase et al. (1998) Biotechnol. Appl. Biochem., 27, 205), and nucleotides (Overberger et al. (1989) J. Polym. Sci. 27. 3589). Further information on incorporation of agents, quantum dots, encapsulated of agents and additives to assist in imaging can be found in U.S. Pat. No. 9,163,331 entitled Electrospun Matrices, herein incorporated in its entirety.

Ex-Vivo Preconditioning Chambers

In addition to self-seeding, cell-free vascular constructs for direct application to repair of natural structures, blood vessels can also be created in a preconditioning chamber as shown in FIG. 5, which is one embodiment of a preconditioning chamber. The dimensions of the chamber are such that it can hold a matrix. Suitable size ranges can range from about 200×200×600 mm, 100×100×300 mm, preferably about 50×50×150 mm. The matrix can be attached to the first and second attachment ends of the vessel. The vessel is operatively linked to a fluid flow system (not shown) that can pump biological fluid through one end of the vessel, through the attached tubular matrix seeded with cells, and through the other end of the vessel in a continuous manner.

The biological fluid can be pumped using any pumping mechanism such as a gear pump. The chamber can further comprise a rotation device that can be used to rotate the chamber at a desired angle for example, by 45°, 90°, 180° and 360°. The rotation device can be manually operated or can be automated such that the chamber is rotated at a desired speed and at a desired time. In other embodiments, the chamber can be a multi-chambered and can house more than one blood vessel. In other embodiments, both the inside and the outside of the matrix can be preconditioned using the preconditioning chamber of the invention. In such embodiments, the chamber is filled with a volume of preconditioning fluid that can cover the attached matrix. The fluid flow of the biological fluid on the outside of the matrix can be controlled by the same or a separate mechanism than the fluid flow on the inside of the matrix. The biological fluid on the outside may be the same as the biological fluid on the inside. Alternatively, the biological fluid on the outside may be the different than the biological fluid on the inside. The fluid flow parameters may be the same for the biological fluid on the inside and the outside, or can be different. The biological fluid can have a composition and viscosity that mimics blood so that the engineered blood vessels are exposed same fluid flow dynamics as native blood vessels. Examples of biological fluids can include any buffer, medium of physiological fluid (e.g., DMEM with 10% FCS). The viscosity of the fluids can be altered by adding high molecular weight proteins such as 100 kDa dextran. Other molecular weight dextrans can also be used. It will be appreciated that the amount of dextran to be used depends on the molecular weight and can range from about 10%, 20%, 30%. 40%, 50%, and 60%. The composition may also be varied by adding other blood like constituents such as salts.

The biological fluid can be moved through the inside surface (lumen) of the attached matrix as a continuous flow, for example with a continuous flow-rate that can be incremented over time to induce a wall shear in the range of about 1 dyne/cm$^2$ to about 30 dynes/cm$^2$. The step of preconditioning the matrix can also involve moving the biological fluid through the inside surface of the attached matrix as a pulsed flow, for example, a pulsed flow that has a pulse-rate which is incremented over time to induce a wall shear in the range of about 10 dynes/cm$^2$ to about 45 dynes/cm$^2$. The pulse-rate can be incremented over time to induce a wall pressure distribution in the engineered blood vessel in the range of about 60 to about 200 mmHg.

EXAMPLES

An off-the-shelf cell-free vascular graft was developed that can repair small diameter vessels using functionalized electrospun vascular constructs. As noted above, FIGS. 2 and 3 show SEM images of bi-layered electrospun vascular constructs. Unlike the cell-based tissue engineered blood vessels, the described technology utilizes host biologic resources and microenvironment to create autologous vascular tissues, a concept known as "in situ tissue regeneration." Biodegradable and biocompatible bi-layered vascular constructs are fabricated with poly(ε-caprolactone) (PCL) polymers and Type I collagen using electrospinning techniques, followed by bioconjugation of functional agents on the luminal surface, namely heparin and endothelial progenitor cell (EPC) specific CD133 antibodies. Immobilization of EPC-specific antibodies and anti-thrombogenic agent (heparin) are able to prevent thrombosis and capture circulating EPCs that facilitate infiltration of host cells into the vascular graft, which eventually develops into mature vascular tissues in vivo.

The functionalized self-seeding vascular constructs can be used for the lower extremity arterial reconstruction for critical limb ischemia due to trauma and focal peripheral artery disease. Vascular reconstruction remains a problematic clinical dilemma for patients of civilian and military trauma alike. Military penetrating injuries often mandate vascular reconstruction for limb salvage. Many of these injuries require the use of vascular constructs to maintain viability of tissues. Currently, the ideal replacement for traumatized vessels in a contaminated military or civilian wound is a patient's own vascular tissue, namely in the form of a vein graft. However, in many instances, suitable vein graft is not available and a prosthetic graft remains the only option. Unfortunately, permanent prosthetic materials continuously present a lifetime risk of thrombosis and infection, leading to graft failure and potentially a limb loss.

A cell-based tissue engineering approach has been demonstrated to be an excellent treatment option in many preclinical studies. However, this approach requires donor tissue biopsy, extensive cell expansion procedures mandating lengthy time and enormous labor efforts, and high costs. In instances where immediate reconstruction is required, this approach is not a viable option. Therefore, an off-the-shelf self-seeding vascular graft developed, described herein, would be an ideal treatment option that can repair small and medium sized vessels.

Bi-layered vascular grafts were formed by electrospinning based on the observation that an increase in fiber diameter of the scaffold increases the pore size of the vascular scaffold, resulting in better smooth muscle cell (SMC) infiltration. In contrast, endothelial cells (ECs) cultured on smaller diameter fibers have developed enhanced cytoskeletal organization and focal adhesion, when compared to their growth on larger diameter fibers. Structurally distinct bi-layered vascular scaffolds were formed by co-electrospinning. Primary electrospinning provides small diameter fibers (300-500 nm) for EC adhesion, and subsequently, the secondary electrospinning produces large diameter fibers (3-5 μm) for SMC infiltration. Controllable parameters of electrospinning include the solution concentration, flow rate, electric field strength, distance between tip and collector, needle tip design, and collector composition and geometry. Varying these parameters controls the fiber morphology, diameter, and alignment of end product.

Figure 9:
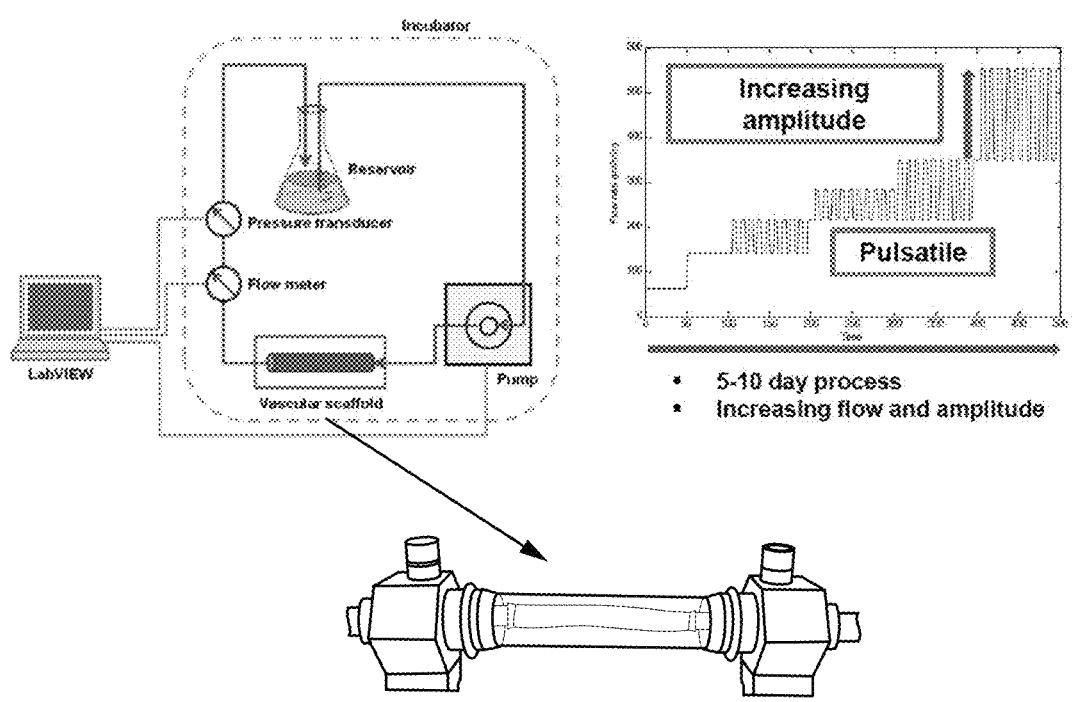
FIG. 9 is a schematic view of a preconditioning chamber or pulsatile bioreactor set-up (top left image) showing a vascular scaffold in position (bottom image). Top right view shows the flow and amplitude parameters used when preconditioning a vascular scaffold.

The bi-layered scaffolds facilitate endothelialization and SMC maturation for improved vascular tissue function. As an alternative to self-seeding (cell-free) constructs, a pulsatile perfusion bioreactor system can be employed to precondition and mature both EC and SMC layers within the bi-layered electrospun scaffold (see FIG. 9). Electrospun vascular scaffolds combined with cells are able to maintain patency and retain structural integrity in a rabbit aorta-iliac bypass model.

Figure 10:
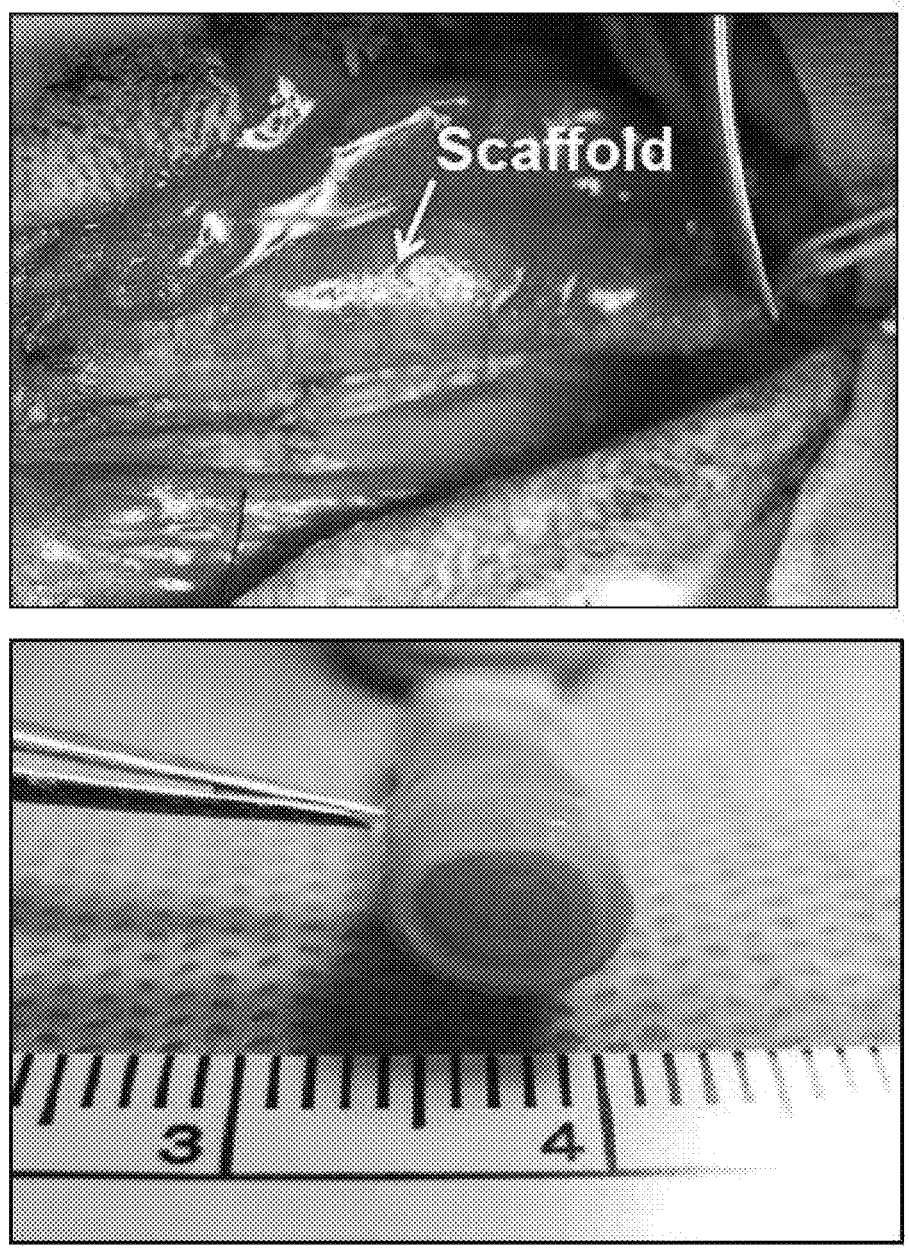
FIG. 10 is a picture of a sheep carotid arterial interposition model. Top image is an end-to-end anastomosis and the bottom image is a retrieved engineered vessel at 6 months.
Figure 11:
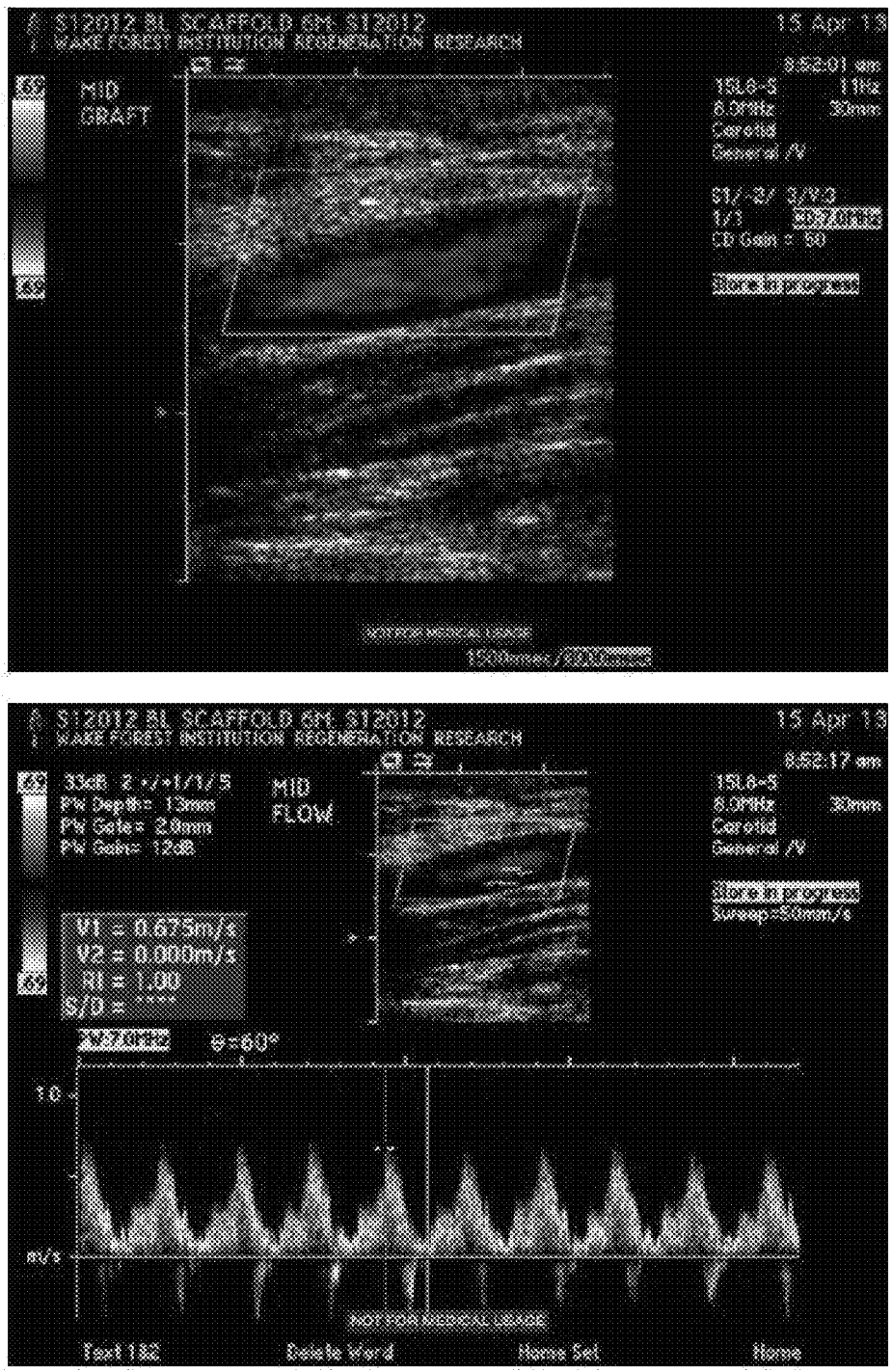
FIG. 11 are ultrasonography images at 6 months.
Figure 12:
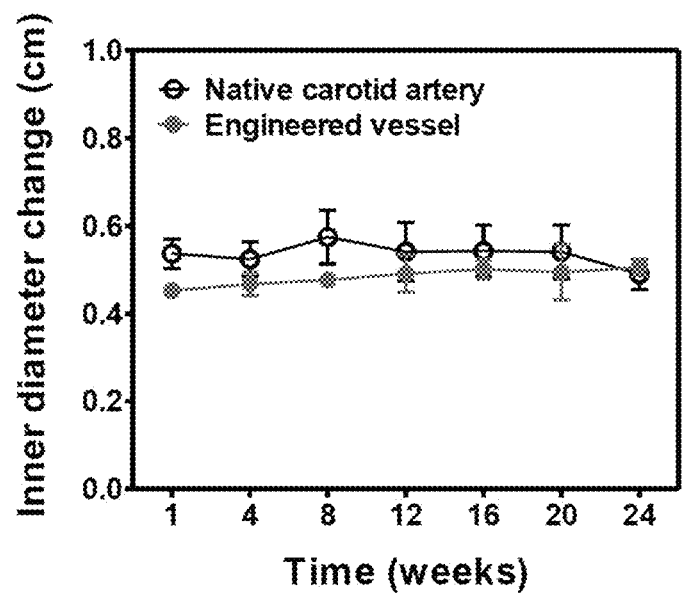
FIG. 12 is a graph of the inner diameter change of engineered vessels over time (top). The bottom image is a contrasted CT scan of an engineered vessel.
Figure 12:
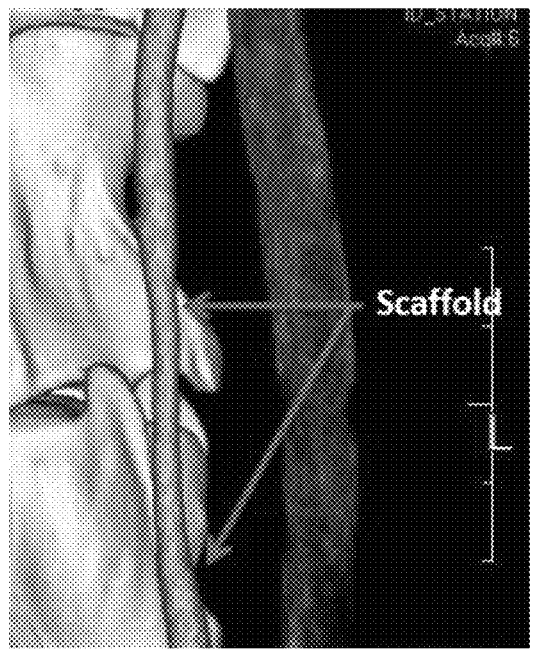

The clinical feasibility using a fully cellularized vascular scaffolding system containing primary ECs and SMCs has been demonstrated in a sheep carotid arterial interposition model. The results show that the cell-seeded vascular scaffolds maintained a high degree of patency and structural integrity without eliciting a histologic inflammatory response over the course of 6-month period (see FIGS. 10, 11, and 12). Moreover, the matured EC coverage on the lumen and thick smooth muscle layer were observed at 6 months. Although these results indicate that cell-based tissue engineered constructs are effective in producing functional blood vessels. this approach requires donor tissue biopsy, extensive cell expansion procedures mandating lengthy time and enormous labor efforts, and high costs.

Figure 13:
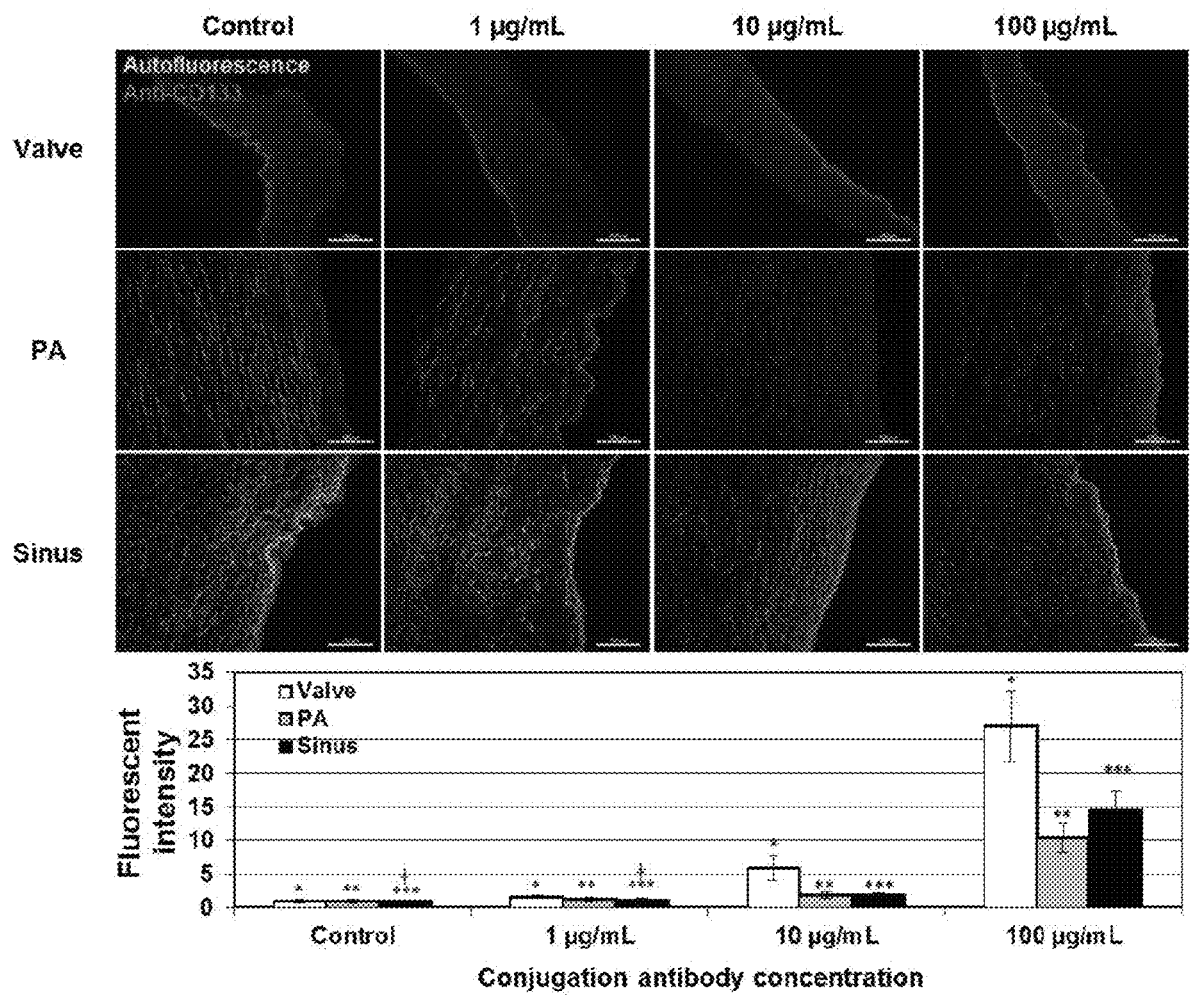
FIG. 13 are fluorescent images of CD133 antibody conjugation in different tissues and a graph of fluorescent intensity vs. conjugated antibody concentration.

To determine whether circulating EPCs can be effectively captured by the cell specific antibodies for in situ endothelialization, EPC specific CD133 antibodies were conjugated on valve tissue leaflets. The effect of varying the CD133 antibodies presented on the antibody surface is displayed in FIG. 13. The results show a qualitative increase in antibody immobilization (red immunofluorescence) as the concentration of CD133 antibody increases. FIG. 13, top 3 rows, show fluorescent images of valve tissue leaflet (valve), pulmonary artery (PA), and sinus (respectively) following anti-CD133 antibody conjugation at various antibody concentrations.

FIG. 13 also shows the relative quantity of anti-CD133 antibody conjugated to valve tissue following anti-CD133 conjugation at various concentrations expressed as fluorescence intensity of fluorophore conjugated secondary antibody per tissue area normalized to autofluorescence intensity. Error bars=SD. *:$p<0.05$ all of the valve tissues were compared to one another, : $p<0.05$ all of the PA tissues were compared to one another, *: $p<0.05$ all of the sinus tissues were compared to one another. 4: $p=0.334$.

Figure 14:
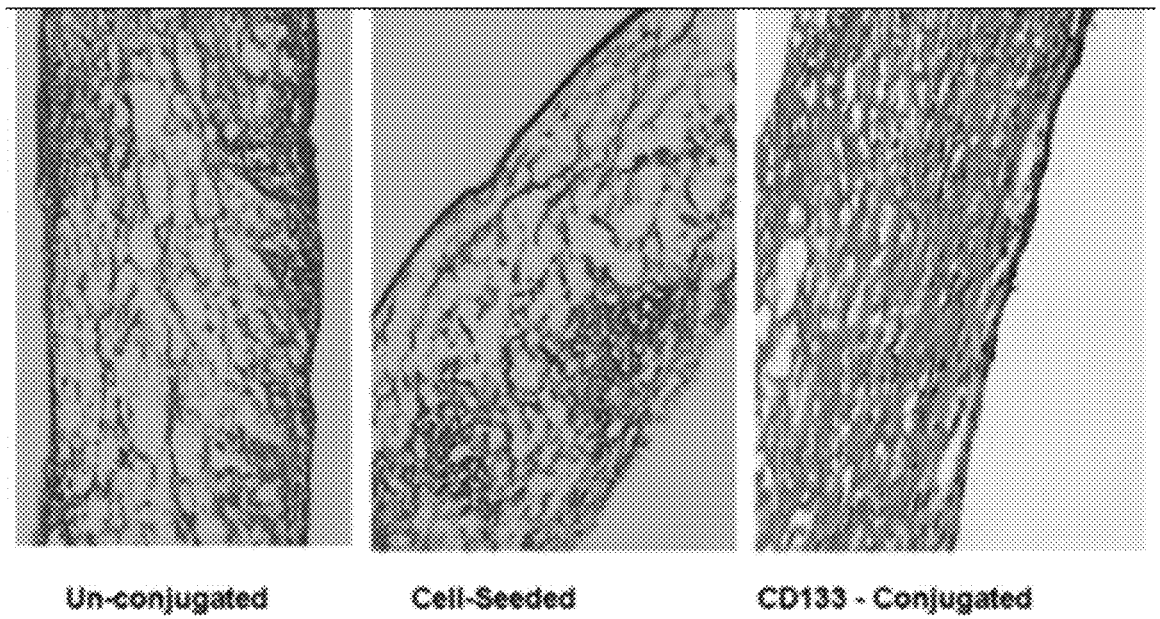
FIG. 14 shows the cell content after 3 months in vivo.

To determine the effect of conjugated EPC specific antibodies in vivo, decellularized porcine pulmonary valves were conjugated with CD133 antibodies, and transplanted into the pulmonary position of sheep. After 1 or 3 months, the implants were removed and assessed for cell and matrix content as well as biomechanical properties. After 1 month in vivo, cells were virtually nonexistent on unconjugated valve leaflets. Despite seeding with EPC-derived endothelial cells before implantation, cell-seeded valves did not display substantially more cells than the unconjugated controls. However, there was clear nuclear staining along the ventricular edge of the leaflet that extended through the lamina radialis into both the lamina spongiosa and fibrosa of conjugated valves. At 3 months, the results were nearly identical in both unconjugated and cell-seeded groups, whereas even more nuclei were distributed throughout the lamina spongiosa and fibrosa of conjugated valves (FIG. 14). In addition to more nuclei, hematoxylin and eosin staining revealed an increase in eosinophilic staining throughout the spongiosa and fibrosa regions, likely owing to increased collagen. To determine the distribution and density of cells in the conjugated valves, we used 4,6-diamino-2-phenylindole staining. Beginning as early as 1 week (determined in 1 animal that died of noncardiac complications), high densities of cells were observed along the edges of the leaflets. By 1 month, this had reached confluence along the ventricular side of the leaflet with increasing cell content across all lamina, but especially within the lamina fibrosa. At 3 months, all layers of the conjugated leaflets were cell-rich and densely populated.

Figure 15:
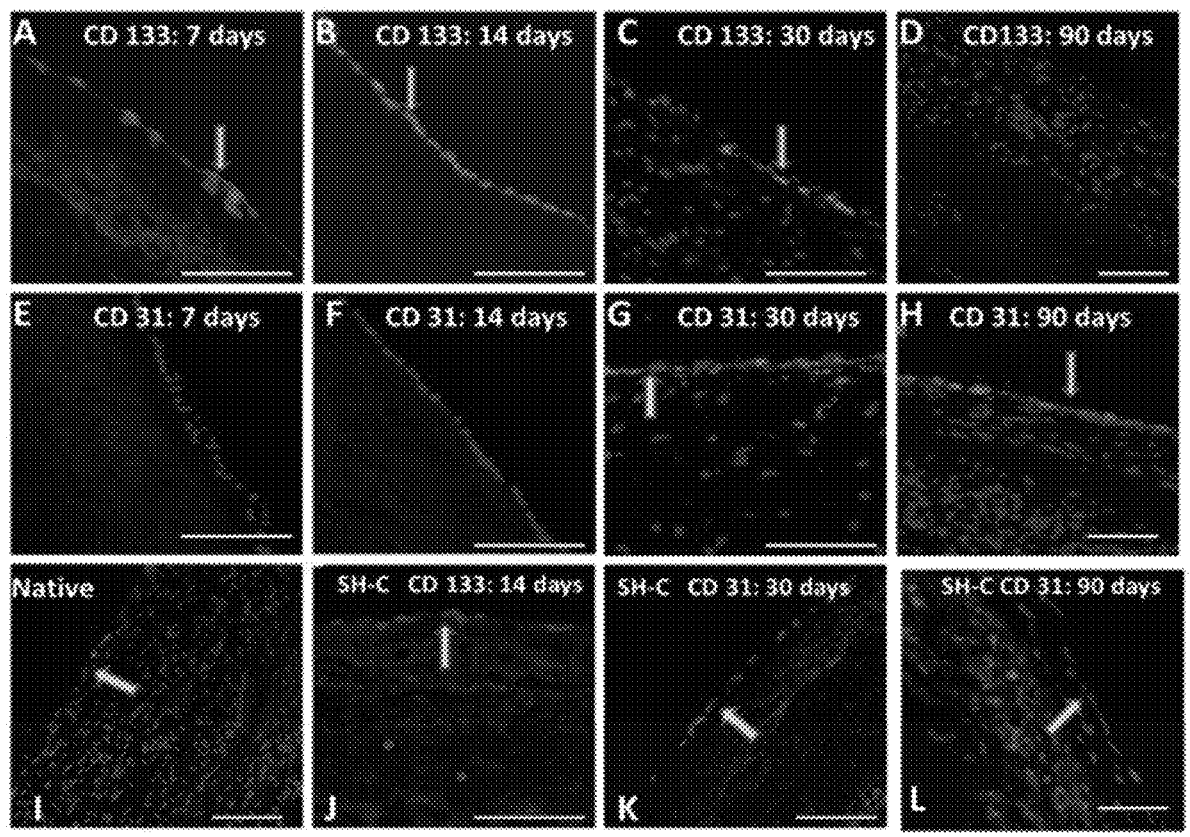
FIG. 15 shows immunohistochemical staining of valve leaflets from CD133-C, SH-C, and native valve leaflets. Secondary antibodies to CD133 or CD31 are Texas Red-labeled. Nuclei are counterstained with DAPI. Top Row: The first row of images depicts leaflets stained for the stem cell marker CD133. There is progressive seeding of the lumen surface with CD133+ cells from 7 days to 30 days post-implantation. CD133 expression decreases around 30 days and is negative at 90 days post implantation. Bottom Row: Conversely, CD31 (a marker for more mature endothelial cells), is strongly expressed 30 days postimplantation, but not earlier (Images E-H). Later expression of CD31 in the conjugated leaflets (Images G and H) is similar to that of native tissue (Image I). Sham conjugated valves failed to develop a confluent CD31+ monolayer even out to 90 days. Arrows point to positive staining for each marker. Images are taken at mid-leaflet between the pulmonary artery insertion and the free margin. Scale bars are 100 μm.

CD133mAb-conjugated decellularized porcine heart valve scaffolds recellularized more quickly and to a greater extent than endothelial cell pre-seeded valve constructs when placed in the pulmonary position of sheep. We performed additional studies to better characterize this recellularization process in vivo. Sham-conjugated (SH-C) or CD133 mAb-conjugated (CD133-C) decellularized porcine heart valve scaffolds were transplanted into 24 sheep and then removed 7. 14, 30, or 90 days after implantation (n=3/construct type/time-point). Cells initially adhering to the leaflet surfaces of CD133 mAb-conjugated constructs were CD133+ and CD31− (FIGS. 15A and 15B vs. 15E and 15F). Arrows point to positive staining for each of the markers. By 30 days post implantation, there were CD133+ and CD31+ (FIGS. 15C and 15G). By 90 days, these cells expressed CD31, but not CD133 (FIGS. 15D and 15H). In contrast, CD133+ cells were not observed adhering to the leaflet surfaces of sham-conjugated valve leaflets until 14 days, and then only in small numbers (FIG. 15J). They expressed CD31 by day 30 and formed a confluent layer by 90 days post-implantation (FIGS. 15K and 15L). Surface (lumen) cells of native leaflets express CD31 (FIG. 15I).

Figure 16A:
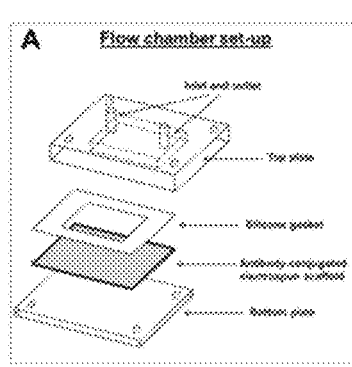
FIG. 16A and FIG. 16B show the flow chamber set-up for measuring circulating capturing capability of EPC-specific antibody-conjugated vascular scaffolds.
Figure 16B:
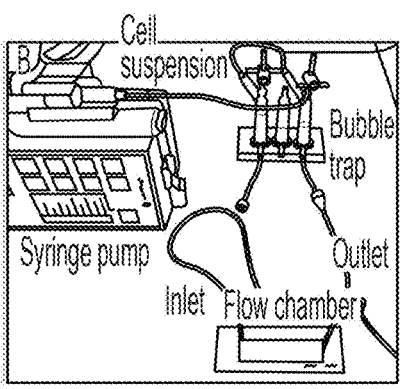
Figure 16C:
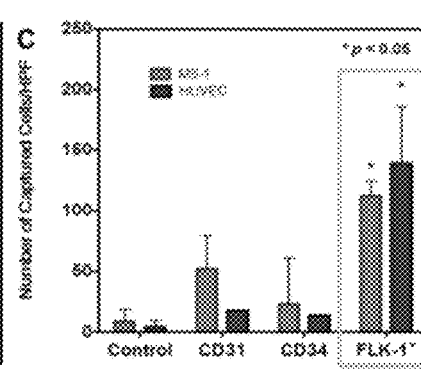
FIG. 16C is a graph of the number of captured cells with different EC antibody-conjugated vascular scaffolds (*P<0.05).
Figure 17A:
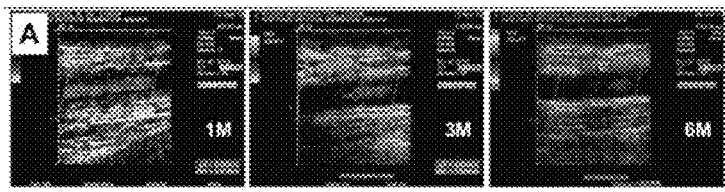
FIG. 17A are ultrasonography images of a sheep carotid arterial interposition model at 1, 3, and 6 months after implantation.
Figure 17B:
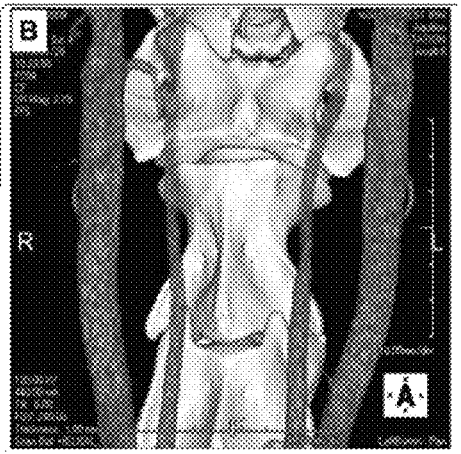
FIG. 17B is a CT image of transplanted graft at 6 months of implantation.
Figure 17C:
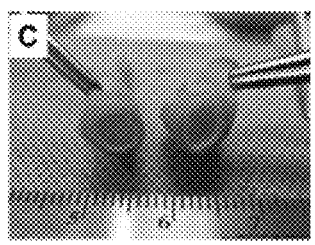
FIG. 17C is an image of the gross appearance of the harvested vascular scaffold at 6 months.
Figure 17D:
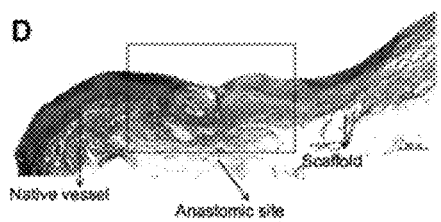
FIG. 17D is a histological image of the harvested vascular scaffold at 6 months.
Figure 17F:
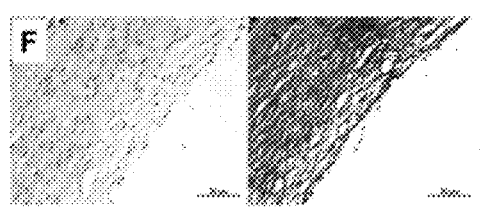
FIG. 17F demonstrate the ECM production: (left) collagen, (right) elastin.
Figure 17E:
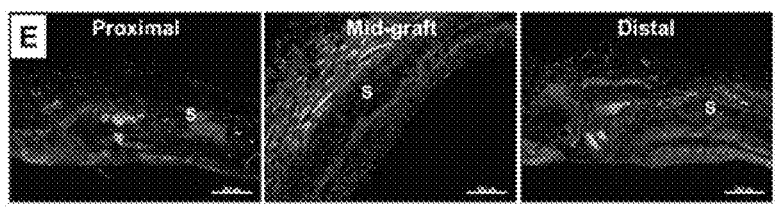
FIG. 17E are immunofluorescence images of the harvested vascular scaffolds at 6 months.

Bioconjugation parameters on the vascular graft have been studied to determine the biological properties and structural configuration that enhance cellular interactions of ECs on the vascular lumen. To assess the functionality, the vascular constructs were examined using a parallel rectangular flow chamber system for cell capturing ability and platelet adhesion for anti-thrombogenic effects (FIGS. 16A and 16B). The results showed that the functionalized vascular constructs, bioconjugated with EPC-specific antibodies (CD31, CD34, and Flk-1) and heparin, are able to achieve an effective capturing of EPC/EC (FIG. 16C) and anti-thrombogenesis. This study demonstrates that generation of the functional vascular grafting system, along with the use of existing tools for selection and directed immobilization of EPC-specific antibodies and anti-thrombogenic agent, is able to provide the necessary components for successful construction of small diameter blood vessels.

Biofunctional bilayered vascular graft with heparin-conjugation have also been demonstrated to provide an initial anti-thrombogenic effect and maintains the required mechanical properties. The vascular scaffold is biocompatible, biodegradable, biomechanically stable, and is able to support vascular cell accommodation. The manufactured vascular scaffolds can also be produced in a variety of dimensions with good consistency in composition and adequate physical properties. We have shown that the bifunctional vascular constructs are able to maintain patency and retain structural integrity with minimal host response during the 6-month of investigation in a sheep model (see FIGS. 17A-17F).

Additionally, as described above, to enhance mobilization of host smooth muscle cells to the implanted vascular scaffold, various growth factor can be added. PDGF-BB and/or SDF-1α were selected for incorporation. First, the growth factors were added to the polymer solution. In some embodiments, the amount of growth factor to be loaded and/or incorporated into the solution was about 0.01-100

μg/mL. Next, the heparinized PCL/collagen scaffolds were electrospun as described above.

Figure 18:
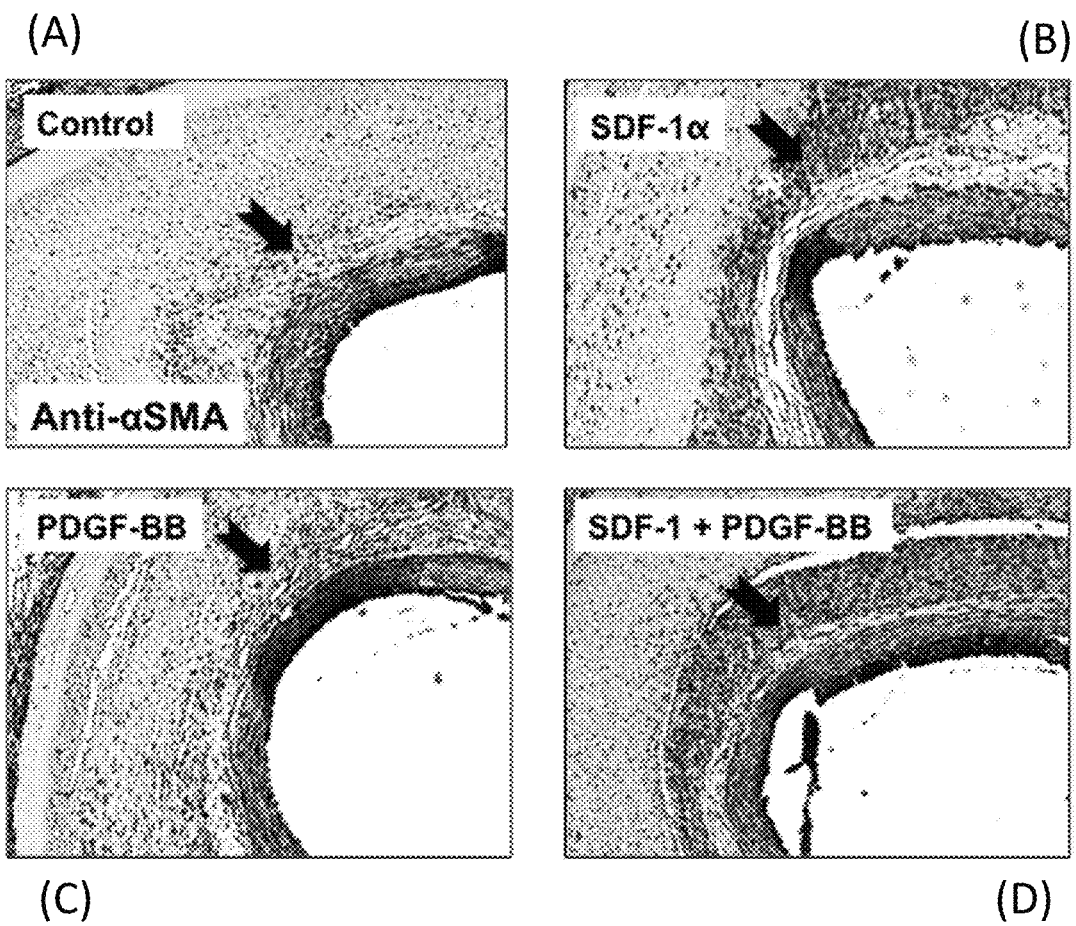
FIG. 18 depicts a histological examination of cell infiltration showing the enhancement of cell recruitment due to incorporating various growth factors into the scaffold when spinning the outer layer of the bilayer scaffold.

The PDGF-BB and/or SDF-1α growth factors were bound to heparinized scaffold via electrostatic interactions. FIG. 18 shows a histological examination of cell infiltration to show the enhancement of cell recruitment due to the incorporation of the various growth factors into the bilayer scaffold. In this example, the polymer solution was electrospun on the inside of a wrapped sheet of smooth muscle cells. FIG. 18 at panel (D) shows the histological results from the hematoxylin and eosin staining of the outer layer when stromal cell-derived factor 1-α and platelet derived growth factor-BB were added to the solution prior to electrospinning. FIG. 18 at panel (D) shows cell density suggesting that a combined effect of these factors in conjunction with chemotaxis can result in recruitment and mobilization of smooth muscle cells to the implanted vascular scaffold.

Thus, the functionalized self-seeding vascular constructs of the present invention have been successfully demonstrated in a sheep model without any noticeable side effects. Since this is a cell-free product, it can be stored at room temperature. Additional product considerations will be tested after the safety and biocompatibility testing.

Other embodiments and uses of the invention will be apparent to those skilled in the art from consideration of the specification and practice of the invention disclosed herein. All U.S. patents and other references noted herein for whatever reason are specifically incorporated by reference. The specification and examples should be considered exemplary only with the true scope and spirit of the invention indicated by the claims.

What is claimed is:

1. A self-seeding vascular graft comprising an electrospun matrix having a hollow tubular shape with an outside surface and a lumen that is defined by an inside surface, the matrix having a three-dimensional ultrastructure of interconnected fibers, the fibers having an average diameter between 100 nanometer and 5 micrometers and wherein at least two different endothelial cell or endothelial progenitor cell (EC/EPC) specific antibodies are conjugated to the inner surface of the matrix.

2. The self-seeding vascular graft of claim 1, wherein the two different EPC-specific antibodies are selected from the group consisting of CD133, CD31, CD34, CD45, CD144, CD146, CD202b, VE-cadherin, VEGF, and Flk-1 antibodies.

3. The self-seeding vascular graft of claim 1, wherein the at least one of the two or more different antibodies is a CD31 antibody.

4. The self-seeding vascular graft of claim 1, wherein the at least one of the two or more different antibodies is a CD133 antibody.

5. The self-seeding vascular graft of claim 1, wherein the at least one of the two or more different antibodies is a VE-cadherin antibody.

6. The self-seeding vascular graft of claim 1, wherein the at least one of the two or more different antibodies is a VEGF antibody.

7. The self-seeding vascular graft of claim 6, wherein the VEGF antibody is a VEGFR3 antibody.

8. The self-seeding vascular graft of claim 1, wherein the graft further comprises one or more anti-thrombogenic agents conjugated to the inner surface of the matrix.

9. The self-seeding vascular graft of claim 8, wherein the one or more anti-thrombogenic agents are selected from the group consisting of heparin, heparin sulfate, low molecular weight heparins and heparin-like compounds.

10. The self-seeding vascular graft of claim 9, wherein the one or more anti-thrombogenic agents comprises heparin.

11. The self-seeding vascular graft of claim 1, wherein the matrix further comprises an inner region, in which the average pore size is less than 1 micron, and an outer region, in which the average pore size is greater than 1 micron.

12. The self-seeding vascular graft of claim 11, wherein the inner region of the tubular matrix comprises fibers having an average diameter between about 100 and about 900 nanometers.

13. The self-seeding vascular graft of claim 11, wherein the outer region of the tubular matrix comprises fibers having an average fiber size of between about 1 micron and about 5 microns.

14. The self-seeding vascular graft of claim 1, wherein the electrospun matrix is formed of fibers comprising at least one natural component.

15. The self-seeding vascular graft of claim 14, wherein the at least one natural component is selected from the group consisting of collagen, fibrin, elastin, laminin, fibronectin, hyaluronic acid, chondroitin 4-sulfate, chondroitin 6-sulfate, dermatan sulfate, heparin sulfate, heparin, and keratan sulfate, and proteoglycans.

16. The self-seeding vascular graft of claim 14, wherein the electrospun matrix comprises collagen.

17. The self-seeding vascular graft of claim 1, wherein the electrospun matrix is formed of fibers comprising at least one synthetic polymer component.

18. The self-seeding vascular graft of claim 17, wherein the at least one synthetic polymer component is selected from the group consisting of poly(ε-caprolactone) (PCL), polylactic acid (PLA), polyglycolic acids (PGA), poly(lactide-co-glycolides) (PLGA), poly(urethanes), poly(siloxanes) or silicones, poly(ethylene), poly(vinyl pyrrolidone), poly(hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), nylons, polyamides, polyanhydrides, poly(ethylene-co-vinyl alcohol) (EVOH) poly(vinyl acetate), polyvinylhydroxide, poly(ethylene oxide) (PEO) and polyorthoesters.

19. The self-seeding vascular graft of claim 17, wherein the electrospun matrix comprises poly(ε-caprolactone) (PCL).

20. A method of preparing a vascular construct by an electrospinning process, the method comprising:
   electrically charging a solution of a matrix material;
   discharging the electrically charged solution onto a grounded target under an electrostatic field to produce fibers of the matrix on the grounded target, wherein the matrix has a tubular shape with an outside surface and a lumen that defines an inside surface and a three-dimensional ultrastructure of interconnected fibers with pores to permit cell attachment;
   manipulating the electrospinning process parameters to vary the porosity of the matrix to form multiple layers having different porosities such that the tubular matrix comprises an inner region, in which the average pore size is less than 1 micron, and an outer region, in which the average pore size is greater than 1 micron; and
   conjugating at least two different EC/EPC-specific antibodies to the inner surface of the matrix.

21. The method of claim 20, wherein the step of conjugating one or more EC/EPC-specific antibodies to a surface of the three-dimensional ultrastructure further comprises activating at least a portion of lumen prior to conjugation with said at least two different antibodies.

22. The method of claim 21, wherein the step of activating at least a portion of lumen further comprises activating at least a portion of the lumen with a carbodiimide agent.

23. The method of claim 21 wherein the step of activating at least a portion of the lumen further comprises immersing the construct in a solution comprising EDC (1-ethyl-3(3-dimethyl aminopropyl) carbodiimide) and NHS (N-hydroxyl-sulfo-succinimide) to form peptide bonds.

24. The method of claim 20, wherein at least a portion of lumen is first functionalized with heparin and then with EC/EPC-specific antibodies.

25. The method of claim 24, wherein a concentration of the heparin on the activated surface is about 0.01-10 mg/mL and a concentration of the antibodies on the activated surface is about 1-1000 µg/mL.

26. The method of claim 20, wherein the at least two different EC/EPC-specific antibodies are selected from the group consisting of CD133, CD31, CD34, CD45, CD144, CD146, CD202b, VE-cadherin, VEGF, and Flk-1 antibodies.

27. The method of claim 26, wherein the EC/EPC-specific antibodies comprise anti-CD31 antibodies.

28. The method of claim 26, wherein the EC/EPC-specific antibodies comprise anti-CD133 antibodies.

29. The method of claim 26, wherein the EC/EPC-specific antibodies comprise anti-VE-cadherin antibodies.

30. The method of claim 26, wherein the EC/EPC-specific antibodies comprise anti-VEGF antibodies.

31. The method of claim 30, wherein the anti-VEGF antibodies further comprise anti-VEGFR3 antibodies.

32. The method of claim 20, wherein the matrix material solution further comprises at least one growth factor.

33. The method of claim 32, wherein the at least one growth factor further comprises at least one of a platelet derived growth factor-BB (PDGF-BB) and/or a stromal cell-derived factor 1-α (SDF-1α).

34. The method of claim 32, wherein a concentration of the at least one growth factor in said matrix material solution is about 0.01-100 µg/mL.

35. The method of claim 20, wherein the method further comprises manipulating the electrospinning process parameters to vary the fiber size such that the inner region of the tubular matrix comprises fibers having an average diameter between 100 and 900 nanometers.

36. The method of claim 20, wherein the method further comprises manipulating the electrospinning process parameters to vary the fiber size such that the the outer region of the tubular matrix comprises fibers having an average fiber size of between about 1 micron and about 5 microns.

* * * * *